US005859312A

United States Patent [19]

Littman et al.

[11] Patent Number: 5,859,312
[45] Date of Patent: Jan. 12, 1999

[54] TRANSGENIC NON-HUMAN ANIMALS HAVING TARGETING ENDOGENOUS LYMPHOCYTE TRANSDUCTION GENES AND COGNATE HUMAN TRANSGENES

[75] Inventors: Daniel Littman; Shinichiro Sawada; Nigel Killeen, all of San Francisco, Calif.

[73] Assignee: The Regents of the University of California, Oakland, Calif.

[21] Appl. No.: 676,828

[22] Filed: Jul. 8, 1996

Related U.S. Application Data

[63] Continuation of Ser. No. 590,051, Jan. 3, 1996, abandoned, which is a continuation of Ser. No. 943,818, Sep. 11, 1992, abandoned.

[51] Int. Cl.$^6$ ............................ C12N 15/00; C07H 21/04; C01N 33/53
[52] U.S. Cl. ............................ 800/2; 435/172.3; 435/7.1; 800/DIG. 1; 536/23.1
[58] Field of Search ...................................... 800/2

[56] References Cited

U.S. PATENT DOCUMENTS 5,530,178 6/1996 Mak ............................................ 800/2

FOREIGN PATENT DOCUMENTS 2 692 435 12/1993 France .......................... A01K 67/027

WO 91/04327 4/1991 WIPO ............................. C12N 15/00

OTHER PUBLICATIONS

Makre et al. I. Immune 146 (8): 2522, 1991.
Diamond et al. PNAS 85:1615, 1988.
Travis Science 256:1392, 1992.
Rohemsella et al. Nature 353:100, 1991.
Killeen et al. FMBO J 11(12): 4329, 1992.
Killeen et al. J. Cell. Biochem, Syrol 14A, 1990 Abstract D 210.
Gross et al. J. Cell Biochem, Syprol 14 B, 1990 Abstract CE 115.

*Primary Examiner*—Suzanne E. Ziska
*Attorney, Agent, or Firm*—Townsend and Townsend and Crew LLP

[57] ABSTRACT

The invention provides transgenic non-human animals and transgenic non-human mammalian cells having at least one functionally disrupted lymphocyte transduction locus, particularly a CD4 locus, targeting constructs used to produce such transgenic stem cells and animals, methods and targeting constructs for inactivating or suppressing expression of endogenous lymphocyte transduction gene loci, transgenes encoding heterologous lymphocyte transduction proteins, and nonhuman animals that express a human lymphocyte transduction protein and lack expression of a cognate murine lymphocyte transduction protein.

8 Claims, 13 Drawing Sheets

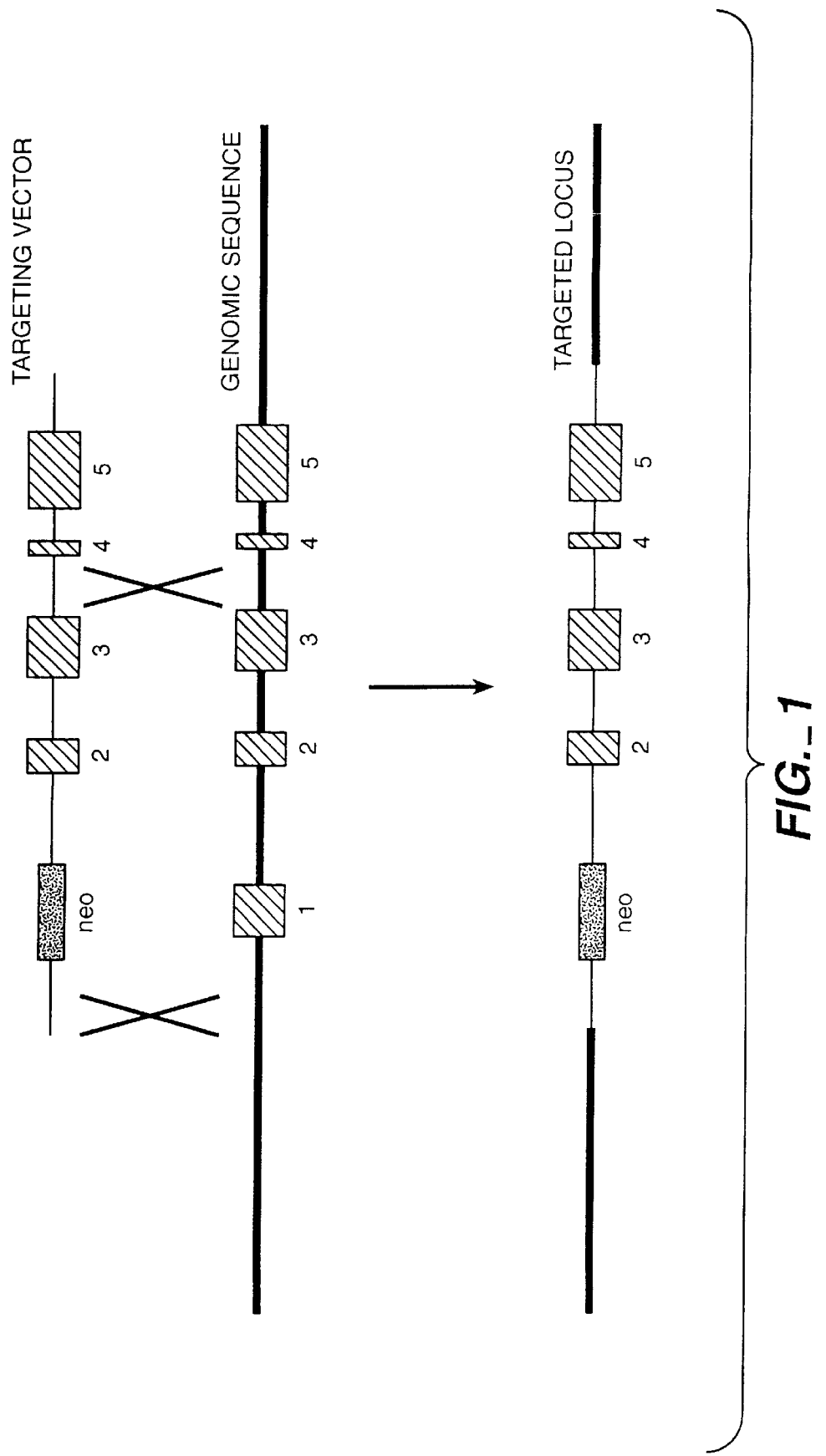
FIG._1

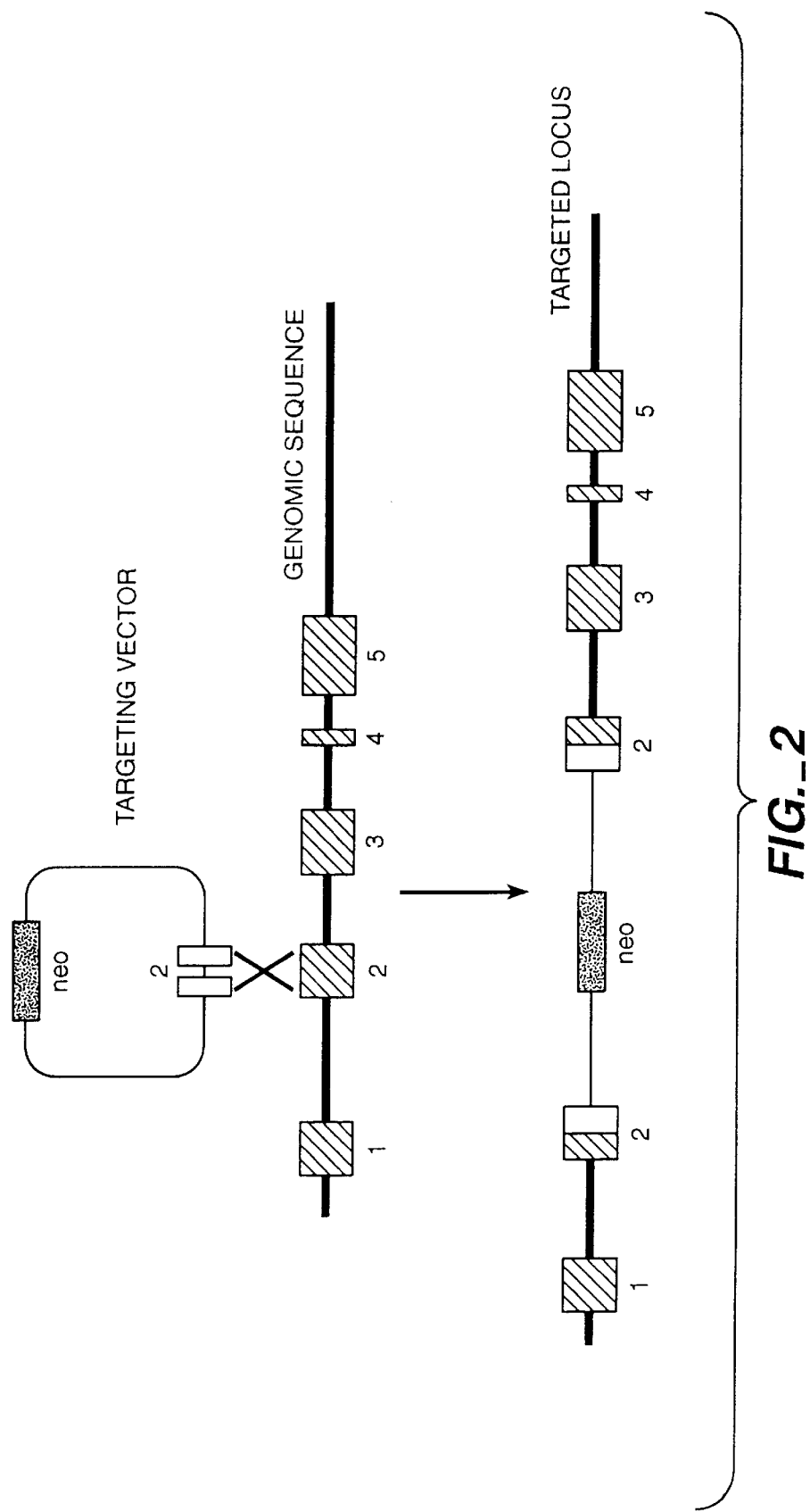
FIG._2

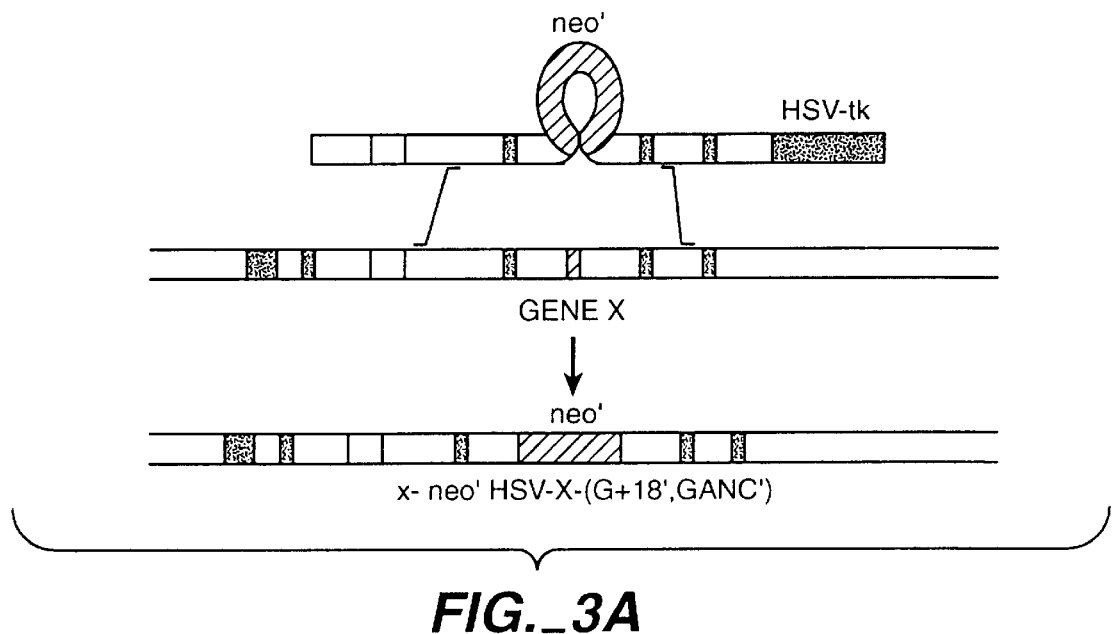
FIG._3A
FIG._3B
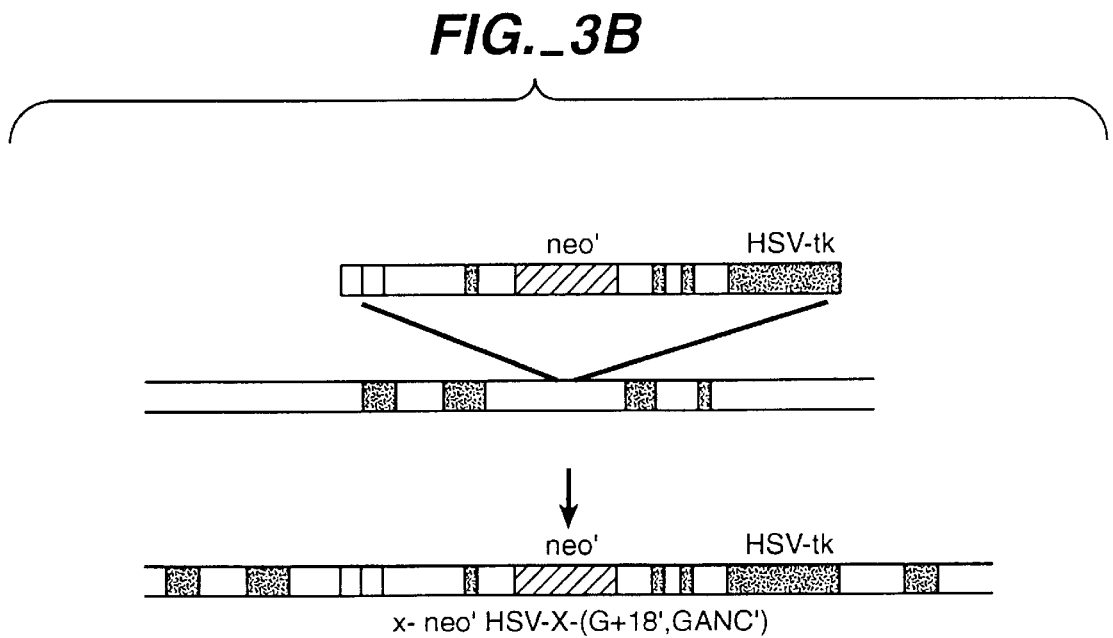

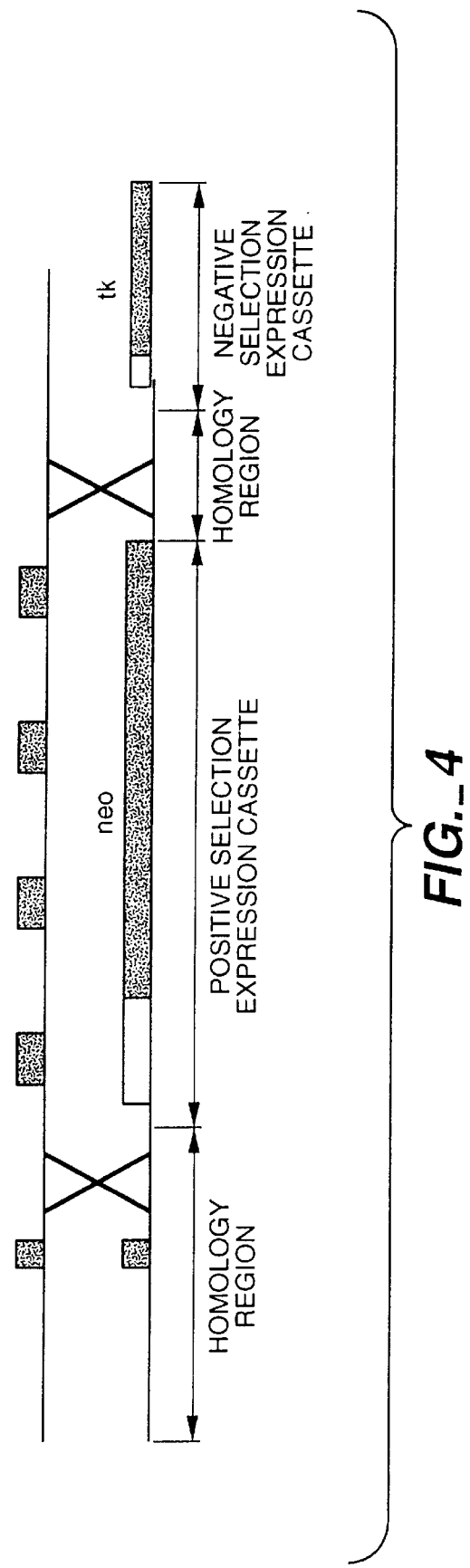
FIG._4

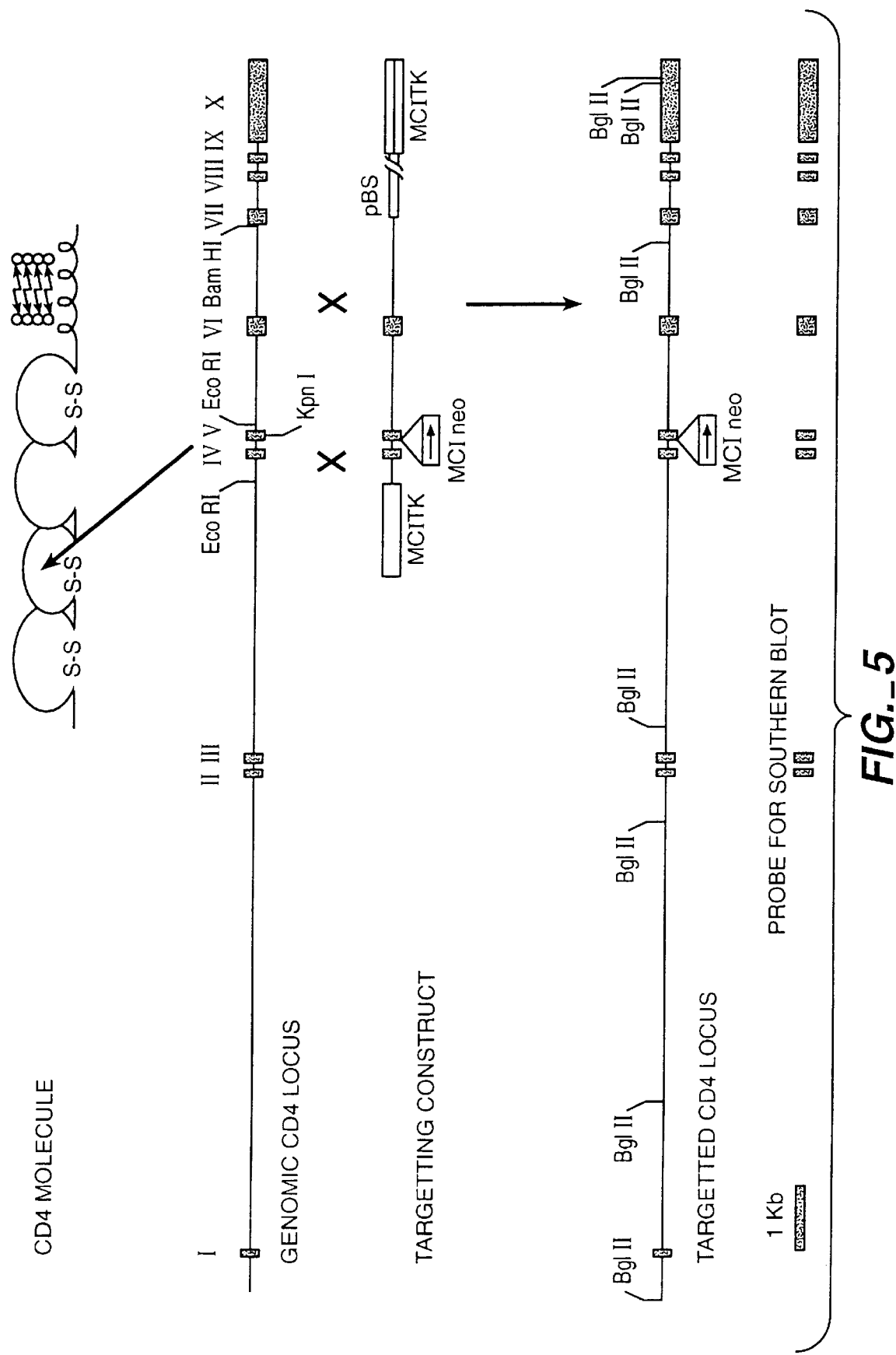
FIG._5

| FEATURES | LOCATION/QUALIFIERS |
|---|---|
| ENHANCER | 79..418 |
| | /NOTE = "MINIMAL ENHANCER" |
| MISC_BINDING | 97..115 |
| | /NOTE = "NUCLEAR PROTEIN BINDING SITE 1" |
| MISC_BINDING | 143..161 |
| | /NOTE = "NUCLEAR PROTEIN BINDING SITE 2" |
| MISC_BINDING | 275..289 |
| | /NOTE = "NUCLEAR PROTEIN BINDING SITE 3" |

ORIGIN     CHROMOSOME 6

```
  1 TATGAACTTG TTTACAGGGC TTCATGGCTC AGAACCTACC CAGAGAATTT
 51 TCTGTTCTAC ATCCCCAACC AAGCCAAGGT GTTGGGGTTC AAATTTGAGC
101 CCCAGCTGTT AGCCCTCTGC AAAGAAAAAA AAAAAAAAAA AAGAACAAAG
151 GGCCTAGATT TCCCTTCTGA GCCCCACCCT AAGATGAAGC CTCTTCTTTC
201 AAGGGAGTGG GGTTGGGGTG GAGGCGGATC CTGTCAGCTT TGCTCTCTCT
251 GTGGCTGGCA GTTTCTCCAA AGGGTAACAG GTGTCAGCTG GCTGAGCCTA
301 GGCTGAACCC TGAGACATGC TACCTCTGTC TTCTCATGGC TGGAGGCAGC
351 CTTTGTAAGT CACAGAAAGT AGCTGAGGGG CTCTGGAAAA AAGACAGCCA
401 GGGTGGAGGT AGATTGGTCC TTCTAGTTGC AGCTTCCAAG GTGCCGCCAG
451 GTCTGGGCGT TCACCCCAC ACCAAGGAGA AGCCTTTGTA ACCCAGCCCA
501 GCTACCGACC CAAGCCCACC CCACAGCTAT TTGCGGGAG TTTCAGTGCT
551 ATAGCAGATG GTTTCTGTAA CGAGGTCACC ACAGGGCTGC ACCTGGTGCT
601 CCACTTCCAT CGTCCTCATC TCTAATACAC TGGCCTCCTC TAGTGCTCTT
651 TTGGCAGCCT CTCACAGTGT CCGGGCCCCT GCTTCCTTTC TCCCATTTGG
701 TCACCTTCCC CTCTTCTAGC TAGAAGCACA GAATATGGAC AGCAAACATA
751 GCTCCAAACA AGAACTAGGA AT
```

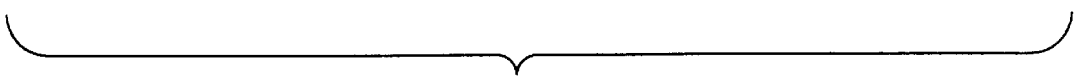

FIG._6

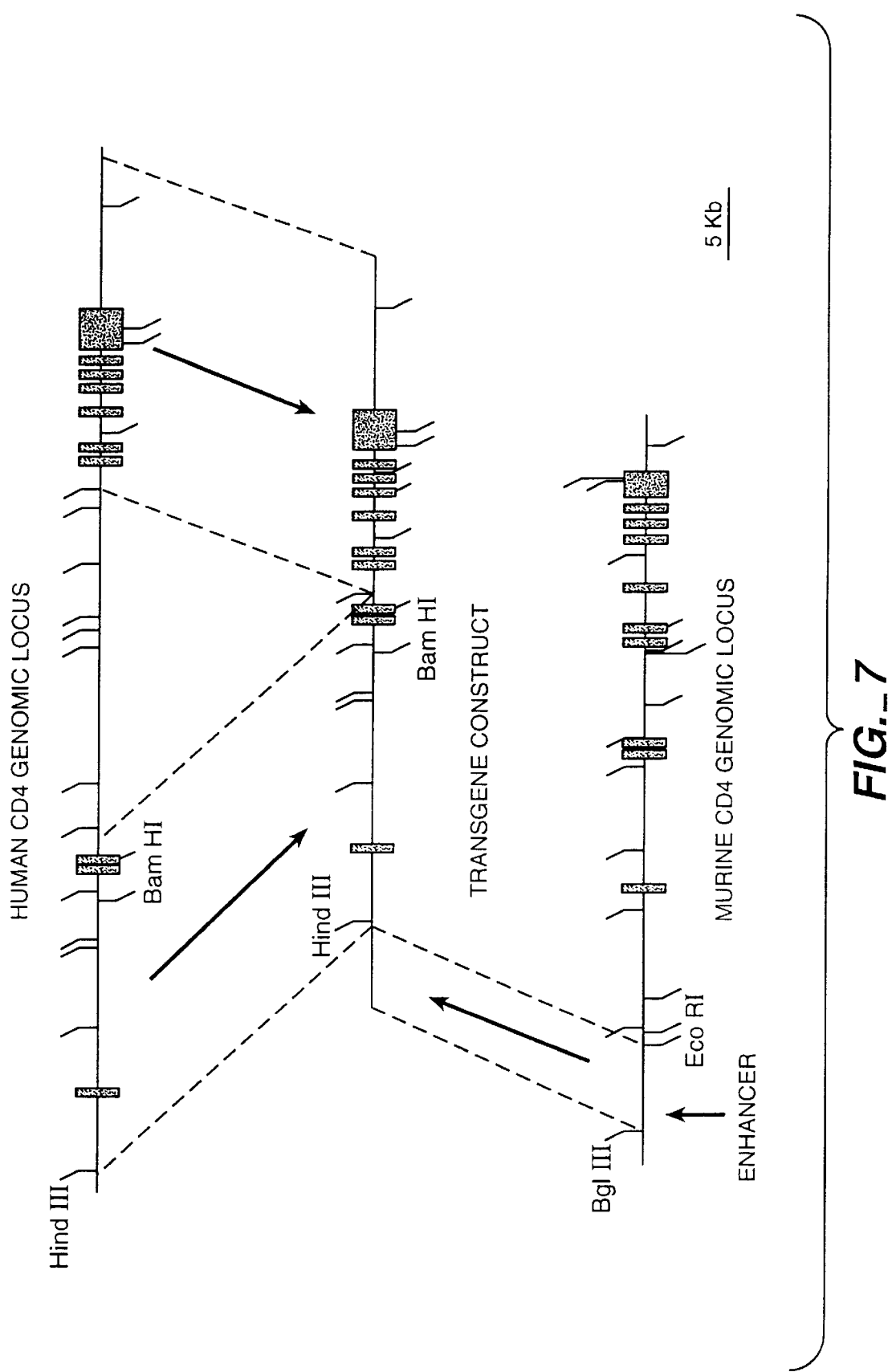
FIG._7

TRANSGENIC NON-HUMAN ANIMALS HAVING TARGETING ENDOGENOUS LYMPHOCYTE TRANSDUCTION GENES AND COGNATE HUMAN TRANSGENES

This is a Continuation of U.S. Ser. No. 08/590,051, filed Jan. 3, 1996, now abandoned, which was a FWC continuation of U.S. Ser. No. 07/943,818, filed Sep. 11, 1992, now abandoned.

TECHNICAL FIELD

The invention provides transgenic non-human animals and transgenic non-human mammalian cells having functionally disrupted lymphocyte transduction gene loci, targeting constructs used to produce such transgenic cells and animals, transgenes encoding human lymphocyte transduction polypeptide sequences, and methods and DNA constructs for inactivating or suppressing expression of endogenous lymphocyte transduction gene loci and for expressing a cognate human transgene. In a preferred embodiment, the endogenous lymphocyte transduction gene is a murine CD4 gene and the transgene encodes a human CD4 gene.

BACKGROUND OF THE INVENTION

Lymphocyte subpopulations (e.g., T cells and B cells) can be distinguished by their biological functions and also by characteristic cell surface proteins which are involved in lymphocyte-specific signal transduction and/or pathogenesis of lymphotropic viruses. Some of these lymphocyte transduction proteins have been identified with specific antibodies. These cell surface antigenic markers are commonly referred to as "cluster of differentiation" or "CD" markers. Moreover, the expression of some of these surface markers correlates with the stage of differentiation of particular lymphocyte subpopulations. Various CD markers have been identified and classified in human and nonhuman lymphocyte populations (see, *Immunology: A Synthesis*, Second Ed., Golub, E. S. and Green, D. R., Eds., Sinauer Associates, Sunderland, Mass., 1991, Appendix 2, incorporated herein by reference). When, for example, a murine marker has been found to be homologous to a particular human marker, both markers receive the same CD designation. Although lymphocyte transduction proteins from various species may share some degree of sequence homology, it is not known whether homologous lymphocyte transduction molecules perform equivalent roles between species or whether homologous lymphocyte transduction molecules are functionally interchangeable.

In addition to correlating with lymphocyte subpopulations, certain CD molecules also have been found to play important roles in transduction of signals for lymphocyte activation and/or in transduction of viral infectivity (e.g., virion attachment and entry) and/or viral pathogenesis. For example, CD2, CD4, and CD8 each play a role in T cell activation, and CD4 also is involved in HIV pathogenesis and may function as a virus receptor for HIV-1. For example, CD4 is expressed on helper T cells and plays an important signalling role during antigen recognition by binding to a nonpolymorphic region of major histocompatibility complex (MHC) class II molecules (Glaichenhaus et al. (1991) *Cell* 64: 511; Littman, D. R. (1987) *Ann. Rev. Immunol.* 5: 561; Parnes, J. R. (1989) *Adv. Immunol.* 44: 265; Barzaga-Gilbert et al. (1992) *J. Exp. Med.* 175: 1707). It is believed that CD4, in conjunction with MHC class II molecules, plays an essential role in the selection of the T cell repertoire during thymic ontogeny (Teh et al. (1991) *Nature* 349: 241; Robey et al. (1991) *Proc. Natl. Acad. Sci. (U.S.A.)* 88: 608). Evidence suggests that CD4 is important in MHC class II recognition, and during antigen recognition CD4 interacts with the T cell antigen receptor-CD3 complex and the lymphocyte-specific tyrosine kinase p56lck (Sancho et al. (1992) *J. Biol. Chem.* 267: 7871; Pelchen-Matthews et al. (1992) *J. Cell. Biol.* 117: 279; Collins et al. (1992) *J. Immunol.* 148: 2159; Haughn et al. (1992) *Nature* 358: 328). The functional association between CD4, p56lck, and other lymphocyte surface molecules such as MHC class II molecules indicates a potential role for $CD4^+$ T cells in mediating autoimmune diseases as well as other immune disorders. The interaction between CD4 and membrane-associated p56lck has also been implicated in HIV-1 pathogenesis (Crise B. and Rose J. K. (1992) *J. Virol.* 66: 2296).

Several CD antigens and other lymphocyte surface molecules are involved in lymphocyte transduction, which comprises activation signal transduction and/or viral transduction in lymphocytes. Lymphocyte activation signal transduction refers to the signal transduction pathway(s) which produce antigenic activation of lymphocytes, from antigen recognition to proliferation of antigen-specific cells and/or acquisition of specific biological functions (e.g., IL-2 expression). For example, the interaction of antigen with the antigen receptor on T lymphocytes initiates an ordered series of pleiotropic changes; a process denoted as T lymphocyte activation. T lymphocyte activation is a 7 to 10 day process that results in cell division and the acquisition of immunological functions such as cytotoxicity and the production of lymphokines that induce antibody production by B lymphocytes and control the growth and differentiation of granulocyte and macrophage precursors. The cytokines produced by activated T lymphocytes act upon other cells of the immune system to coordinate their behavior and bring about an effective immune response.

The initiation of T lymphocyte activation requires a complex interaction of the antigen receptor with the combination of antigen and self-histocompatibility molecules on the surface of antigen-presenting cells. T lymphocytes may also be activated by relatively simple stimuli such as the combination of a calcium ionophore (e.g., ionomycin) and an activator of protein kinase C, such as phorbol myristate acetate (PMA). Several lectins, including phytohemagglutinin (PHA) may also be used to activate T cells (Nowell, *Cancer Res.* 20:462–466 (1960)). T lymphocyte activation involves the specific regulation of particular subsets of genes. The transcriptional regulation characteristic of T cell activation begins minutes after the antigen encounter and continues until at least 10 days later. The T lymphocyte activation genes can be grouped according to the time after stimulation at which each gene is transcribed. Early genes are the first subset of T lymphocyte activation genes that is expressed during the activation process. Expression of the early genes triggers the transcriptional modulation of subsequent genes in the activation pathway.

CD8 is expressed on the surface of cytotoxic T cells and function in signal transduction of antigen recognition by MHC class I-specific T cell receptors (TCRs). CD2 is expressed on the surface of T cells and mediates adhesion of T cells to antigen-presenting cells (APCs) by interacting with the APC surface molecule LFA-3, facilitating antigen recognition by T cells. CD3 forms a complex with the T cell receptor which binds specific antigen as a primary step in antigenic activation of T cells.

Helper and cytotoxic subsets of T lymphocytes can be distinguished by their surface expression of the CD4 and/or CD8 glycoproteins. Immature thymocytes show a coordinate expression of both CD4 and CD8, but mature lymphocytes express either CD4 or CD8, but not both. Thus, the repression of either CD4 or CD8 may be a pivotal event in the differentiation of T cells into functionally distinct subsets. CD4 expression is associated with T helper lymphocytes, whereas CD8 expression is associated with T cytotoxic lymphocytes. Both CD4 and CD8 are considered to be members of the immunoglobulin gene superfamily on the basis of sequence homology, but not on the basis of biological function. CD4 is a 55 kD glycoprotein having a extracellular domain that is 372 amino acids long composed of four tandem Ig-like VJ regions, a 23 amino acid long transmembrane domain, and a 38 amino acid long cytoplasmic domain. CD8 generally exists as a heterodimer of two disulfide-linked subunits, α (34–38 kD) and β (30–35 kD), or as α—α homodimers.

Besides antigenic activation of T cells, lymphocyte transduction may alternatively or additionally comprise viral transduction in lymphocytes, wherein a lymphocyte transduction protein is necessary for efficient expression of a viral-induced phenotype in a lymphocyte or lymphocyte population. For example, CD4 is involved in the pathogenesis of HIV-1 in producing acquired immune deficiency syndrome (AIDS) and other HIV-induced immune system disorders. Although CD4 has been proposed as a receptor for attachment and infectious entry of HIV virions into $CD4^+$ T cells, CD4 may also function in transducing HIV-induced signals to a $CD4^+$ T cell by a mechanism that does not require infection of the T cell by HIV-1 (Groux et al. (1992) J. Exp. Med. 175: 331).

Some other CD antigens also have been shown to be targets for adsorption and entry of lymphotropic viruses. For example, CD21 mediates infection of human B lymphocytes with the Epstein-Barr virus (EBV) (Hedrick et al. (1992) Eur. J. Immunol. 22: 1123). The gp120 envelope glycoprotein of HIV binds to the human CD4 molecule on the surface of T lymphocytes and some macrophage-monocytes and appears to mediate internalization of the HIV virion (Arthos, J. et al. (1989) Cell 57: 469). Indeed, HIV infection is characterized by a dramatic decline in the number of $CD4^+$ T cells, which may result in some of the pathological changes noted in AIDS (e.g., opportunistic infections, increased incidence of neoplasms). Neither HIV nor EBV infect mouse lymphocytes and thus there are presently no convenient nonhuman models for studying these viral infections or resultant immune system effects, such as the immunodeficiency of HIV infection which is characterized by deletion of $CD4^+$ lymphocytes. It may not be necessary for HIV to infect T cells in order to produce pathogenesis; HIV virions and/or HIV-infected T cells may produce pathological effects on uninfected T cells (particularly helper T cells) by a non-infective mechanism (e.g., depletion of helper T cells may occur without the cells being infected with HIV). However, it appears that HIV-related pathological effects can be produced in T cells bearing human CD4 molecules, but not in nonhuman T cells which lack human CD4 (Groux et al. (1992) op.cit.). Thus, nonhuman models expressing human lymphocyte transduction proteins would be highly desirable for studying human immunodeficiencies and human viral pathogenesis.

CD44 participates in a wide variety of cell-cell interactions including lymphocyte homing and tumor metastasis (Jackson et al. (1992) J. Biol. Chem. 267: 4732). CD25 is the β chain of the IL-2 receptor. Several other T cell-specific membrane-associated proteins that are involved in lymphocyte activation and/or lymphotropic viral pathogenesis have also been identified and cloned (Weissman et al. (1988) Science 239: 1028; Hedrick et al (1984) Nature 308: 149; Chien et al (1984) Nature 312: 31).

In addition to several of the recognized CD antigens which have been defined by specific antibodies, other proteins function in lymphocyte activation and/or viral pathogenesis. For example, the lymphocyte-specific p56lck tyrosine kinase interacts with CD4 and participates in T cell activation and HIV-1 viral pathogenesis (Crise B. and Rose J. K. op.cit.; Collins op.cit.; Cefai et al. (1992) J. Immunol. 149: 285; Caron et al. (1992) Mol. Cell. Biol. 12: 2720). Molina et al. (1992) Nature 357: 161, report that thymocyte development is inhibited by an absence of functional p56lck protein. Other membrane-associated tyrosine kinases (e.g., p53/56lyn, p59fyn) may also participate in lymphocyte signal transduction (Campbell M. A. and Sefton B. M. (1992) Mol. Cell. Biol. 12: 2315).

Gene targeting, mediated by homologous recombination between a targeting polynucleotide construct and a homologous chromosomal sequence, has been used to disrupt several genes, including the HPRT gene, β2-microglobulin gene, int-2 proto-oncogene, and the fos proto-oncogene (Thomas and Cappechi (1987) Cell 51: 503; Zijlstra et al. (1989) Nature 342: 435; Mansour et al. (1988) Nature 336: 348; and Johnson et al. (1989) Science 245: 1234: Adair et al. (1989) Proc. Natl. Acad. Sci (U.S.A.) 86:4574; Capecchi, M. (1989) TIG 5:70; Capecchi, M. (1989) Science 244:1288). Mansour et al. (1988) op.cit. have described homologous targeting constructs that include a HSV tk gene that permits negative selection against nonhomologous integration events in conjunction with positive selection for integrated transgenes.

Transgenic nonhuman mammalian cells and transgenic nonhuman animals which harbor one or more inactivated genes required for production of functional lymphocyte transduction molecules, such as CD4, are desirable as experimental model systems and as hosts for expression of transgenes encoding heterologous (e.g., human) cell surface proteins. Kucherlapati (WO91/10741) discusses strategies for producing non-human mammalian hosts characterized by inactivated endogenous immunoglobulin loci. Lonberg (WO92/03918) describes construction of vectors for targeting endogenous immunoglobulin loci and inactivation of endogenous immunoglobulin genes with such targeting vectors. Rahemtulla et al. (1991) Nature 353: 180, describes disruption of an endogenous murine CD4 gene by homologous gene targeting in embryonic stem cells. Jasin et al. (1990) Genes Devel. 4: 157, report targeting the human CD4 gene in a T lymphoma cell line by epitope addition. Koh et al. (1992) Science 256: 1210, report disruption of an endogenous murine CD8 gene by homologous gene targeting in ES cells. Molina et al. (1992) op.cit., describes disruption of the murine lck gene, which encodes a tyrosine kinase implicated in signal transduction by CD4 and CD8. Grusby et al. (1991) Science 253: 1417, describes disruption of the MHC Class II $A^b$ beta gene by gene targeting in mice; the resultant targeted mice are reported to be depleted of $CD4^+$ lymphocytes.

Animals having a functionally disrupted endogenous lymphocyte transduction gene and also harboring a transgene which expresses a heterologous (i.e., derived from a different species) lymphocyte transduction gene product would be useful as models for studying disease pathogenesis and fundamental immunology, as well as providing useful models for screening for novel therapeutic agents to treat viral infection, autoimmune diseases, and immunosuppression. For example, nonhuman animals in which helper T cell development is dependent on expression of human CD4 would be useful for studies of several human diseases in which the function of CD4+ T cells is altered.

Based on the foregoing, it is clear that a need exists for nonhuman cells and nonhuman animals harboring one or more functionally disrupted endogenous lymphocyte transduction genes and also harboring a transgene encoding a cognate human lymphocyte transduction polypeptide which is expressed in at least a subset of host lymphocytes. Thus, it is an object of the invention herein to provide targeting transgenes for inactivating, by homologous recombination, endogenous lymphocyte transduction genes, particularly the CD4 gene. It is also an object of the invention to provide methods to produce transgenic nonhuman cells and transgenic nonhuman animals harboring correctly targeted homologously recombined transgenes of the invention.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

In accordance with the foregoing objects, in one aspect of the invention targeting constructs are provided which contain at least one portion having a sequence that is substantially homologous to a sequence present in or flanking a lymphocyte transduction gene locus and which, when integrated at the corresponding lymphocyte transduction gene locus, functionally disrupt expression of lymphocyte transduction molecules from the gene locus. Such targeting constructs, or portions thereof, integrate at the lymphocyte transduction gene locus by homologous recombination between the endogenous gene locus and the targeting construct, and cells harboring correctly integrated targeting constructs are selected for and identified by screening according to the methods described herein. In one embodiment, the targeting constructs delete all or a portion of an endogenous lymphocyte transduction gene by a "hit-and-run" strategy, wherein the resultant functionally disrupted lymphocyte transduction locus comprises a deletion and does not comprise an integrated selectable marker. In an alternative embodiment, an endogenous lymphocyte transduction gene is functionally disrupted by a targeting construct which inserts a sequence, typically into a coding sequence (i.e., exon), wherein the resultant disrupted lymphocyte transduction gene is substantially incapable of expressing a functional lymphocyte transduction protein. The invention also provides targeting constructs which functionally disrupt an endogenous lymphocyte transduction gene by targeted site-specific point mutation(s), such as to create a missense or nonsense codon in a coding sequence or ablate a splice signal or transcriptional element sequence. In a preferred embodiment of the invention, an endogenous lymphocyte transduction locus, such as CD4, CD8, or CD2, is functionally disrupted.

The invention also provides targeting constructs that contain at least one portion having a sequence that is substantially homologous to a sequence present in or flanking a lymphocyte transduction gene locus, and which serves as a template for gene conversion of the corresponding endogenous lymphocyte transduction gene locus. Such targeted gene conversion results in the converted (i.e., mutated by gene conversion) endogenous lymphocyte transduction locus being functionally disrupted (i.e., inactivated) and incapable of directing the efficient expression of functional lymphocyte transduction molecules. The invention also provides mammalian cells and nonhuman animals harboring inactivated lymphocyte transduction genes that result from correctly targeted gene conversion. Nucleotide sequences that result from correctly targeted gene conversion generally are not naturally-occurring sequences in the genome(s) of mammals, so a sequence resulting from targeted gene conversion is generally distinguishable from naturally-occurring mutant lymphocyte transduction alleles in the host cell or host animal species. A preferable lymphocyte transduction gene for functional disruption by gene conversion is the CD4 gene.

The invention also provides targeting constructs which replace, by homologous recombination, at least a portion of an endogenous lymphocyte transduction gene with a corresponding portion of a heterologous lymphocyte transduction gene. Such replacements may be partial, yielding a hybrid lymphocyte transduction gene composed partially of endogenous coding and/or regulatory sequences and partially of heterologous lymphocyte transduction gene sequences, or total, wherein the endogenous lymphocyte transduction gene is replaced by a heterologous lymphocyte transduction gene. In some embodiments, the heterologous lymphocyte transduction gene sequences comprise deletions of nonessential sequences, such as intronic sequences, and are referred to as lymphocyte transduction minigenes. For example, the invention provides a human CD4 minigene which can be transcribed and translated in a nonhuman host (e.g., mouse) to produce a functional human CD4 glycoprotein which is developmentally expressed in the same way as an endogenous host CD4 gene. Such a human CD4 minigene may comprise part of a targeting construct or may be separately introduced as a transgene.

The invention also provides nonhuman animals and cells which harbor at least one integrated targeting construct that functionally disrupts an endogenous lymphocyte transduction gene locus, typically by deleting or mutating a genetic element (e.g., exon sequence, splicing signal, promoter, enhancer) that is required for efficient functional expression of a complete gene product. In one embodiment, disruption of an endogenous CD4 gene locus may be accomplished by replacement of a portion of the endogenous CD4 gene with a portion of a heterologous CD4 gene (e.g., a human CD4 gene sequence) by homologous recombination or gene conversion. In an alternative embodiment, a targeting construct is employed to functionally disrupt an endogenous CD4 gene by homologous recombination, and a transgene encoding and expressing a heterologous CD4 molecule is separately introduced into the host genome at a nonhomologous site.

The invention also provides transgenes which encode a lymphocyte transduction gene product that is heterologous to a nonhuman host species. Such transgenes typically comprise a lymphocyte transduction expression cassette, wherein a linked promoter and, preferably, an enhancer drive expression of structural sequences encoding a heterologous lymphocyte transduction protein. For example, the invention provides transgenes which comprise a murine CD4 enhancer and a human CD4 promoter linked to structural sequences that encode a human CD4 protein. Transgenic mice harboring such transgenes express human CD4 in developmental patterns and at levels which are comparable with expression patterns and levels of mouse CD4 in normal nontransgenic mice. Preferably, the polynucleotide sequence encoding the heterologous lymphocyte transduction molecule is operably linked to cis-acting transcriptional regulatory regions (e.g., promoter, enhancer) so that a heterologous lymphocyte transduction protein is expressed in a subset of lymphocytes in a manner similar to the expression of the cognate endogenous lymphocyte transduction in naturally-occurring lymphocyte populations. Thus, it is generally preferable to operably link a lymphocyte transduction encoding sequence to transcriptional regulatory elements which naturally occur in or near the cognate lymphocyte transduction gene (e.g., a T cell-specific enhancer element located upstream of the CD4 transcription initiation site). However, transgenes encoding heterologous lymphocyte transduction proteins may be targeted adjacent to endogenous transcriptional regulatory sequences, so that the operable linkage of a regulatory sequence occurs upon integration of the transgene into a targeted endogenous chromosomal location.

The invention also provides transgenic nonhuman animals harboring at least one endogenous CD4 gene that is inactivated by a targeted genetic modification produced by contacting the endogenous CD4 gene with a targeting construct of the invention. Such contacting of a targeting construct with an endogenous CD4 sequence generally involves electroporation, lipofection, microinjection, calcium phosphate precipitation, biolistics, or other polynucleotide transfer method known in the art.

The invention also provides mammalian cells that express an endogenous CD4 gene, but which have portions of the expressed endogenous CD4 gene deleted or mutated. For example but not limitation, an endogenous CD4 gene can be modified by deleting specific, predetermined exons from germline DNA with one or more targeting constructs, with preferable deletions being those having boundaries approximately the same as boundaries for structural and/or functional domains of the CD4 protein (e.g., tandem Ig-like VJ regions). In an alternative embodiment, predetermined exons or structural domains of an endogenous CD4 gene may be replaced, by homologous targeting, with corresponding portions of a heterologous CD4 gene to generate a hybrid CD4 gene.

The invention also provides transgenic nonhuman animals, such as a non-primate mammal, that have at least one inactivated endogenous CD4 gene, and preferably are homozygous for inactivated CD4 alleles, and which are substantially incapable of directing the efficient expression of endogenous CD4. For example, in a preferred embodiment, a transgenic mouse is homozygous for inactivated endogenous CD4 alleles and is substantially incapable of producing murine CD4 encoded by a endogenous (i.e., naturally-occurring) CD4 gene. Such a transgenic mouse, having inactivated endogenous CD4 genes, is a preferred host recipient for a transgene encoding a heterologous CD4 molecule, preferably a human CD4 molecule which is expressed so that murine lymphocytes having human CD4 molecules on the cell surface are produced. For example, human CD4 may be encoded and expressed from a heterologous transgene(s) in such transgenic mice. Such heterologous transgenes may be integrated in a nonhomologous location in a chromosome of the nonhuman animal, or may be integrated by homologous recombination or gene conversion into a nonhuman CD4 gene locus, thereby effecting simultaneous knockout of the endogenous CD4 gene (or segment thereof) and replacement with the human CD4 gene (or segment thereof).

BRIEF DESCRIPTION OF THE DRAWINGS

FIG. 1 shows a schematic representation of a double crossover replacement recombination event.

FIG. 2 shows a schematic representation of an insertion crossover recombination event.

FIG. 3 shows schematically how positive-negative selection is used to select gene targeting by homologous recombination from random integration.

FIG. 4 is a schematic representation of a positive-negative targeting transgene of the invention.

FIG. 5 shows restriction maps of the murine genomic CD4 locus, a targeting construct, and a correctly targeted murine CD4 locus.

FIG. 6 is the sequence containing a murine CD4 enhancer element.

FIG. 7 graphically represents a human CD4 minigene construct of the invention in comparison to a human CD4 gene locus and a murine CD4 gene locus.

DEFINITIONS

Figure 8:
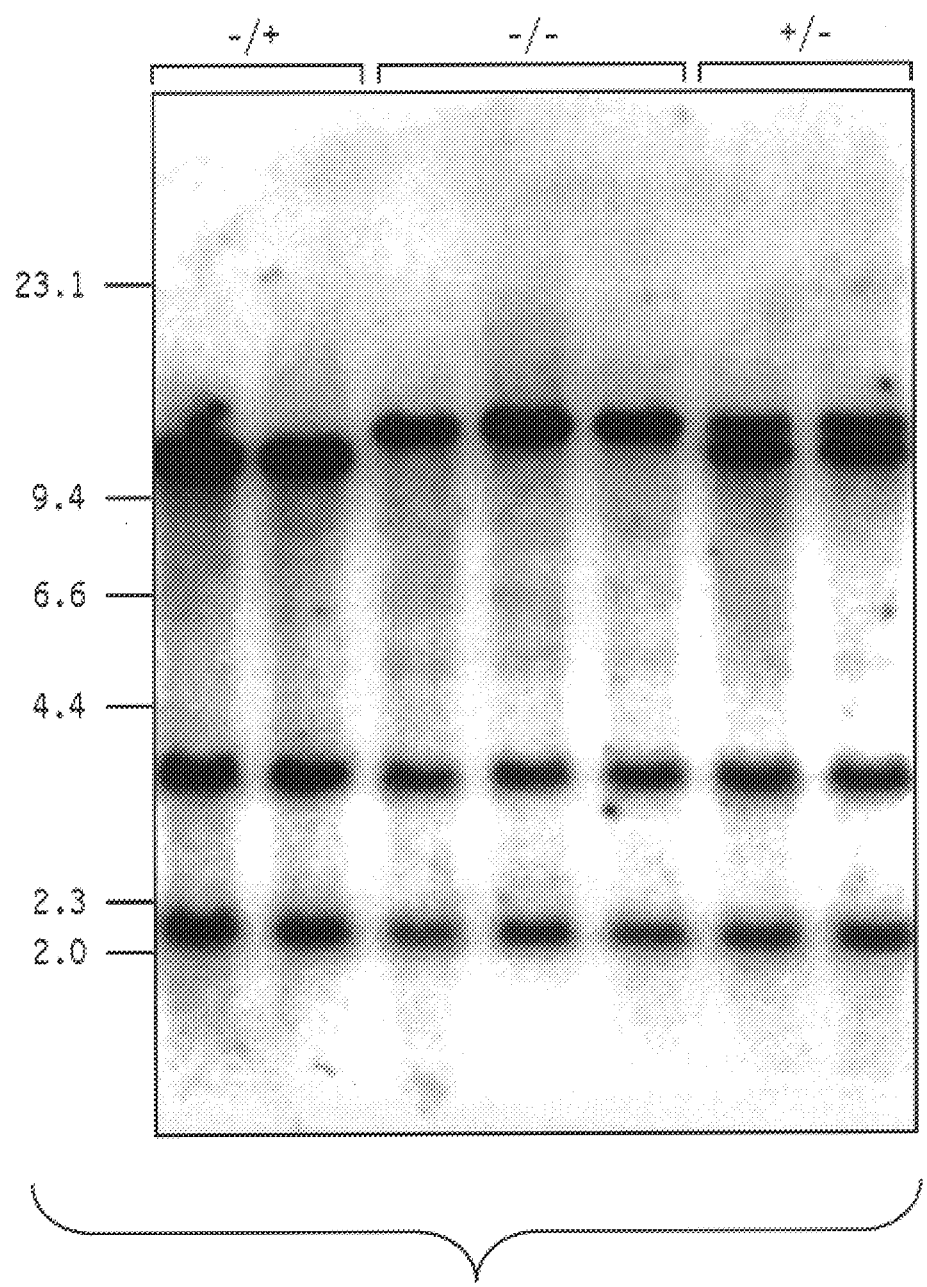
FIG. 8 is an autoradiograph of a Southern blot of a BglII digest of genomic DNA from CD4-targeted mice probed with the probe shown in FIG. 5 showing the 1.2 kb increase in size noted in the approximately 10 kb band in the –/– and +/– mouse DNA.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

"Lymphocyte transduction protein" as used herein, refers to a lymphocyte-specific protein which is required for efficient antigenic activation of lymphocytes (e.g., T cells) or for pathogenesis of a lymphotropic virus. Lymphocyte transduction proteins generally are membrane-associated proteins present on the surface of T lymphocytes or T lymphocyte subsets, such as helper T cells or cytotoxic T cells. As used herein, the term "lymphocyte transduction protein" does not encompass immunoglobulins (i.e., heavy chain, κ chain, λ chain), but can encompass proteins having sequence homology to immunoglobulin sequences (e.g., CD4, T-cell receptor α and β gene products). Examples of lymphocyte transduction proteins include several CD antigens, such as CD2, CD3, CD4, CD8, CD21, CD25, CD28, CD44, and CD45. CD21 is present on B cells but is a receptor for the lymphotropic Epstein-Barr virus, and thus is also a lymphocyte transduction protein.

As used herein, the term "lymphocyte transduction gene" or "lymphocyte transduction gene locus" refers to a region of a chromosome spanning all of the exons which potentially encode a lymphocyte transduction polypeptide and extending through flanking sequences (e.g., including promoters, enhancers, etc.) that participate in lymphocyte transduction protein expression. Thus, a CD4 gene locus includes the region spanning from the first exon through the last exon and also includes adjacent flanking sequences (e.g., polyadenylation signals) that participate in CD4 gene expression (generally at least about 20 to 100 kilobases). Preferred lymphocyte transduction genes that are targeted by the constructs and methods of the invention are: CD2, CD3, CD4, CD8, CD21, CD25, CD28, CD44, and CD45, although essentially any gene encoding a membrane-associated protein involved in differentiation of hematopoietic cells, and particularly in lymphocyte differentiation and activation, may be targeted. Lymphocyte transduction genes that encode proteins that act as viral receptors and/or are involved in lymphocyte activation are especially preferred targets for endogenous gene inactivation and, if desired, for subsequent incorporation of a transgene encoding a cognate heterologous lymphocyte transduction protein. A particularly preferred lymphocyte transduction gene of the invention is the CD4 gene, as it functions both in differentiation of T cell subsets (e.g., helper, T cells), T cell activation, and as a receptor for pathogenesis by HIV-1 and HIV-1-infected cells. The p56lck gene product of the lck gene is involved with CD4-mediated T cell activation and HIV-1 pathogenesis and can be targeted, and, if desired, replaced with a cognate heterologous p56lck gene or minigene.

The terms "functional disruption" or "functionally disrupted" as used herein means that a gene locus comprises at least one mutation or structural alteration such that the functionally disrupted gene is substantially incapable of directing the efficient expression of functional gene product. For example but not limitation, an endogenous CD4 gene that has a neo gene cassette integrated into an exon (e.g., the fifth exon) of a CD4 gene, is not capable of encoding a functional CD4 protein and is therefore a functionally disrupted CD4 gene locus. Also for example, a targeted mutation in the exons of an endogenous heavy chain gene may result in a mutated endogenous CD4 gene that can express a truncated CD4 protein. Functional disruption can include the complete substitution of a heterologous CD4 gene locus in place of an endogenous CD4 locus, so that, for example, a targeting transgene that replaces the entire mouse CD4 locus with the human CD4 locus, which may be functional in the mouse, is said to have functionally disrupted the endogenous murine CD4 locus by displacing it. Deletion or interruption of essential transcriptional regulatory elements, polyadenylation signal(s), splicing site sequences will also yield a functionally disrupted gene. Functional disruption of an endogenous lymphocyte transduction gene, such as a CD4 gene, may also be produced by other methods (e.g., antisense polynucleotide gene suppression). The term "structurally disrupted" refers to a targeted gene wherein at least one structural (i.e., exon) sequence has been altered by homologous gene targeting (e.g., by insertion, deletion, point mutation(s), and/or rearrangement). Typically, lymphocyte transduction alleles that are structurally disrupted are consequently functionally disrupted, however lymphocyte transduction alleles may also be functionally disrupted without concomitantly being structurally disrupted, i.e., by targeted alteration of a non-exon sequence such as ablation of a promoter. An allele comprising a targeted alteration that interferes with the efficient expression of a functional gene product from the allele is referred to in the art as a "null allele".

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The terms "substantially corresponds to", "substantially homologous", or "substantial identity" as used herein denotes a characteristic of a nucleic acid sequence, wherein a nucleic acid sequence has at least about 70 percent sequence identity as compared to a reference sequence, typically at least about 85 percent sequence identity, and preferably at least about 95 percent sequence identity as compared to a reference sequence. The percentage of sequence identity is calculated excluding small deletions or additions which total less than 25 percent of the reference sequence. The reference sequence may be a subset of a larger sequence, such as a portion of a gene or flanking sequence, or a repetitive portion of a chromosome. However, the reference sequence is at least 18 nucleotides long, typically at least about 30 nucleotides long, and preferably at least about 50 to 100 nucleotides long. "Substantially complementary" as used herein refers to a sequence that is complementary to a sequence that substantially corresponds to a reference sequence. In general, targeting efficiency increases with the length of the targeting transgene portion (i.e., homology region) that is substantially complementary to a reference sequence present in the target DNA (i.e., crossover target sequence). In general, targeting efficiency is optimized with the use of isogenic DNA homology clamps, although it is recognized that the presence of various recombinases may reduce the degree of sequence identity required for efficient recombination.

The term "nonhomologous sequence", as used herein, has both a general and a specific meaning; it refers generally to a sequence that is not substantially identical to a specified reference sequence, and, where no particular reference sequence is explicitly identified, it refers specifically to a sequence that is not substantially identical to a sequence of at least about 50 contiguous bases at a targeted endogenous lymphocyte transduction gene, such as a CD4 gene.

Specific hybridization is defined herein as the formation of hybrids between a targeting transgene sequence (e.g., a polynucleotide of the invention which may include substitutions, deletion, and/or additions) and a specific target DNA sequence (e.g., a CD4 gene sequence), wherein a labeled targeting transgene sequence preferentially hybridizes to the target such that, for example, a single band corresponding to a restriction fragment of a genomic lymphocyte transduction gene can be identified on a Southern blot of DNA prepared from cells using said labeled targeting transgene sequence as a probe. It is evident that optimal hybridization conditions will vary depending upon the sequence composition and length(s) of the targeting transgene(s) and endogenous target(s), and the experimental method selected by the practitioner. Various guidelines may be used to select appropriate hybridization conditions (see, Maniatis et al., *Molecular Cloning: A Laboratory Manual* (1989), 2nd Ed., Cold Spring Harbor, N.Y. and Berger and Kimmel, *Methods in Enzymology, Volume* 152. *Guide to Molecular Cloning Techniques* (1987), Academic Press, Inc., San Diego, Calif., which are incorporated herein by reference.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. As used herein, laboratory strains of rodents which may have been selectively bred according to classical genetics are considered naturally-occurring animals.

The term "cognate" as used herein refers to a gene sequence that is evolutionarily and functionally related between species. For example but not limitation, in the human genome, the human CD4 gene is the cognate gene to the mouse CD4 gene, since the sequences and structures of these two genes indicate that they are highly homologous and both genes encode a protein which functions in signaling T cell activation through MHC class II-restricted antigen recognition. Similarly, the human CD2 gene (e.g., GenBank sequence files: Humcd21, Humcd22, Humcd23, Humcd24, and Humcd25) is the cognate human gene to the mouse CD2 gene (e.g., GenBank sequence files: Muscd21, Muscd22, Muscd23, Muscd24, and Muscd25); both CD2 genes share a high degree of sequence homology, have similar intron-exon patterns, and both function to activate T cells by interacting with LFA-3 on antigen-presenting cells, albeit in a species-specific manner. Thus, the term "lymphocyte transduction gene" as used herein refers generically to any human gene encoding a lymphocyte transduction protein known in the art, and also refers to the cognate lymphocyte transduction gene in nonhuman mammal species.

As used herein, a "heterologous gene" or "heterologous CD4" is defined in relation to the transgenic nonhuman organism producing such a gene product. A heterologous polypeptide, also referred to as a xenogeneic polypeptide, is defined as a polypeptide having an amino acid sequence or an encoding DNA sequence corresponding to that of a cognate gene found in an organism not consisting of the transgenic nonhuman animal. Thus, a transgenic mouse harboring a human CD4 gene can be described as harboring a heterologous lymphocyte transduction gene. A transgene containing various gene segments encoding a heterologous protein sequence may be readily identified, e.g. by hybridization or DNA sequencing, as being from a species of organism other than the transgenic animal. For example, expression of human CD4 amino acid sequences may be detected in the transgenic nonhuman animals of the invention with antibodies specific for human CD4 epitopes encoded by human CD4 gene segments. A cognate heterologous gene refers to a corresponding gene from another species; thus, if murine CD4 is the reference, human CD4 is a cognate heterologous gene (as is porcine, ovine, or rat CD4, along with CD4 genes from other species).

As used herein, the term "targeting construct" refers to a polynucleotide which comprises: (1) at least one homology region having a sequence that is substantially identical to or substantially complementary to a sequence present in a host cell endogenous lymphocyte transduction gene locus, and (2) a targeting region which becomes integrated into an host cell endogenous lymphocyte transduction gene locus by homologous recombination between a targeting construct homology region and said endogenous lymphocyte transduction gene locus sequence. If the targeting construct is a "hit-and-run" or "in-and-out" type construct (Valancius and Smithies (1991) *Mol. Cell. Biol.* 11: 1402; Donehower et al. (1992) *Nature* 356: 215; (1991) *J. NIH Res.* 3: 59; which are incorporated herein by reference), the targeting region is only transiently incorporated into the endogenous lymphocyte transduction gene locus and is eliminated from the host genome by selection. A targeting region may comprise a sequence that is substantially homologous to an endogenous lymphocyte transduction gene sequence and/or may comprise a nonhomologous sequence, such as a selectable marker (e.g., neo, tk, gpt). The term "targeting construct" does not necessarily indicate that the polynucleotide comprises a gene which becomes integrated into the host genome, nor does it necessarily indicate that the polynucleotide comprises a complete structural gene sequence. As used in the art, the term "targeting construct" is synonymous with the term "targeting transgene" as used herein.

The terms "homology region" and "homology clamp" as used herein refer to a segment (i.e., a portion) of a targeting construct having a sequence that substantially corresponds to, or is substantially complementary to, a predetermined endogenous lymphocyte transduction gene sequence, which can include sequences flanking said lymphocyte transduction gene. A homology region is generally at least about 100 nucleotides long, preferably at least about 250 to 500 nucleotides long, typically at least about 1000 nucleotides long or longer. Although there is no demonstrated theoretical minimum length for a homology clamp to mediate homologous recombination, it is believed that homologous recombination efficiency generally increases with the length of the homology clamp. Similarly, the recombination efficiency increases with the degree of sequence homology between a targeting construct homology region and the endogenous target sequence, with optimal recombination efficiency occurring when a homology clamp is isogenic with the endogenous target sequence. The terms "homology clamp" and "homology region" are interchangeable as used herein, and the alternative terminology is offered for clarity, in view of the inconsistent usage of similar terms in the art. A homology clamp does not necessarily connote formation of a base-paired hybrid structure with an endogenous sequence. Endogenous lymphocyte transduction gene sequences that substantially correspond to, or are substantially complementary to, a transgene homology region are referred to herein as "crossover target sequences" or "endogenous target sequences."

As used herein, the term "correctly targeted construct" refers to a portion of the targeting construct which is integrated within or adjacent to an endogenous crossover target sequence, such as a portion of an endogenous CD4 gene locus. For example but not limitation, a portion of a targeting transgene encoding neo and flanked by homology regions having substantial identity with endogenous CD4 gene sequences flanking the first exon, is correctly targeted when said transgene portion is integrated into a chromosomal location so as to replace, for example, the first exon of the endogenous CD4 gene. In contrast and also for example, if the targeting transgene or a portion thereof is integrated into a nonhomologous region and/or a region not within about 50 kb of a CD4 gene sequence, the resultant product is an incorrectly targeted transgene. It is possible to generate cells having both a correctly targeted transgene(s)

and an incorrectly targeted transgene(s). Cells and animals having a correctly targeted transgene(s) and/or an incorrectly targeted transgene(s) may be identified and resolved by PCR and/or Southern blot analysis of genomic DNA.

As used herein, the term "targeting region" refers to a portion of a targeting construct which becomes integrated into an endogenous chromosomal location following homologous recombination between a homology clamp and an endogenous lymphocyte transduction gene sequence. Typically, a targeting region is flanked on each side by a homology clamp, such that a double-crossover recombination between each of the homology clamps and their corresponding endogenous lymphocyte transduction gene sequences results in replacement of the portion of the endogenous lymphocyte transduction gene locus by the targeting region; in such double-crossover gene replacement targeting constructs the targeting region can be referred to as a "replacement region". However, some targeting constructs may employ only a single homology clamp (e.g., some "hit-and-run"-type vectors, see, Bradley et al. (1992) *Bio/Technology* 10: 534, incorporated herein by reference).

As used herein, the term "replacement region" refers to a portion of a targeting construct flanked by homology regions. Upon double-crossover homologous recombination between flanking homology regions and their corresponding endogenous lymphocyte transduction gene crossover target sequences, the replacement region is integrated into the host cell chromosome between the endogenous crossover target sequences. Replacement regions can be homologous (e.g., have a sequence similar to the endogenous lymphocyte transduction gene sequence but having a point mutation or missense mutation), nonhomologous (e.g., a neo gene expression cassette), or a combination of homologous and nonhomologous regions.

As used herein, the term "minigene" refers to a heterologous gene construct wherein one or more nonessential segments of a lymphocyte transduction gene are deleted with respect to the naturally-occurring lymphocyte transduction gene. Typically, deleted segments are intronic sequences of at least about 500 basepairs to several kilobases, and may span up to several tens of kilobases or more. Isolation and manipulation of large (i.e., greater than about 30–100 kilobases) targeting constructs is frequently difficult and may reduce the efficiency of transferring the targeting construct into a host cell. Thus, it is frequently desirable to reduce the size of a targeting construct by deleting one or more nonessential portions of a lymphocyte transduction gene. Typically, intronic sequences that do not encompass essential regulatory elements may be deleted. For example, a CD4 minigene may comprise a deletion of an intronic segment between the third and fourth exons of the human CD4 gene. Frequently, if convenient restriction sites bound a nonessential intronic sequence of a cloned lymphocyte transduction gene sequence, a deletion of the intronic sequence may be produced by: (1) digesting the cloned DNA with the appropriate restriction enzymes, (2) separating the restriction fragments (e.g., by electrophoresis), (3) isolating the restriction fragments encompassing the essential exons and regulatory elements, and (4) ligating the isolated restriction fragments to form a minigene wherein the exons are in the same linear order as is present in the germline copy of the naturally-occurring lymphocyte transduction gene. Alternate methods for producing a minigene will be apparent to those of skill in the art (e.g., ligation of partial genomic clones which encompass essential exons but which lack portions of intronic sequence). Most typically, the gene segments comprising a minigene will be arranged in the same linear order as is present in the germline lymphocyte transduction gene, however, this will not always be the case. Some desired regulatory elements (e.g., enhancers, silencers) may be relatively position-insensitive, so that the regulatory element will function correctly even if positioned differently in a minigene than in the corresponding germline gene. For example, an enhancer may be located at a different distance from a promoter, in a different orientation, and/or in a different linear order. For example, an enhancer that is located 3' to a promoter in germline configuration might be located 5' to the promoter in a minigene. Similarly, some lymphocyte transduction genes may have exons which are alternatively spliced at the RNA level, and thus a minigene may have fewer exons and/or exons in a different linear order than the corresponding germline lymphocyte transduction gene and still encode a functional gene product. A cDNA encoding a lymphocyte transduction gene product may also be used to construct a minigene. However, since it is generally desirable that the heterologous lymphocyte transduction minigene be expressed similarly to the cognate naturally-occurring nonhuman lymphocyte transduction gene, transcription of a cDNA minigene typically is driven by a linked lymphocyte transduction gene promoter and enhancer.

DETAILED DESCRIPTION

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, cell culture, and transgene incorporation (e.g., electroporation, microinjection, lipofection). Generally enzymatic reactions, oligonucleotide synthesis, and purification steps are performed according to the manufacturer's specifications. The techniques and procedures are generally performed according to conventional methods in the art and various general references which are provided throughout this document. The procedures therein are believed to be well known in the art and are provided for the convenience of the reader. All the information contained therein is incorporated herein by reference.

Chimeric targeted mice are derived according to Hogan, et al., *Manipulating the Mouse Embryo: A Laboratory Manual*, Cold Spring Harbor Laboratory (1988) and *Teratocarcinomas and Embryonic Stem Cells: A Practical Approach*, E. J. Robertson, ed., IRL Press, Washington, D.C., (1987) which are incorporated herein by reference.

Embryonic stem cells are manipulated according to published procedures (*Teratocarcinomas and Embryonic Stem Cells: A Practical Approach*, E. J. Robertson, ed., IRL Press, Washington, D.C. (1987); Zjilstra et al., *Nature* 342: 435–438 (1989); and Schwartzberg et al., *Science* 246: 799–803 (1989), each of which is incorporated herein by reference).

Oligonucleotides can be synthesized on an Applied Bio Systems oligonucleotide synthesizer according to specifications provided by the manufacturer.

All sequences referred to herein by GenBank database file designation (e.g., GenBank: Humatct4a) are incorporated herein by reference and are publicly available.

In general, the invention encompasses methods and polynucleotide constructs which are employed for generating nonhuman transgenic animals having at least one endogenous lymphocyte transduction gene functionally disrupted and, in some embodiments, also harboring at least one cognate heterologous lymphocyte transduction gene capable of expression.

Gene Targeting

Gene targeting, which is a method of using homologous recombination to modify a mammalian genome, can be used to introduce changes into cultured cells. By targeting a gene of interest in embryonic stem (ES) cells, these changes can be introduced into the germlines of laboratory animals to study the effects of the modifications on whole organisms, among other uses. The gene targeting procedure is accomplished by introducing into tissue culture cells a DNA targeting construct that has a segment homologous to a target locus and which also comprises an intended sequence modification (e.g., insertion, deletion, point mutation). The treated cells are then screened for accurate targeting to identify and isolate those which have been properly targeted. A common scheme to disrupt gene function by gene targeting in ES cells is to construct a targeting construct which is designed to undergo a homologous recombination with its chromosomal counterpart in the ES cell genome. The targeting constructs are typically arranged so that they insert additional sequences, such as a positive selection marker, into coding elements of the target gene, thereby functionally disrupting it. Targeting constructs usually are insertion-type or replacement-type constructs (Hasty et al. (1991) *Mol. Cell. Biol.* 11: 4509, incorporated herein by reference). FIG. 1 shows a typical replacement-type targeting event, and FIG. 2 shows a typical insertion-type targeting event.

Targeting of Endogenous Lymphocyte Transduction Genes

The invention encompasses methods to produce nonhuman animals (e.g., non-primate mammals) that have endogenous lymphocyte transduction marker genes (i.e., at least one lymphocyte transduction locus) inactivated by gene targeting with a homologous recombination targeting construct. Typically, such nonhuman animals have at least a CD4 gene locus functionally disrupted, and may have multiple lymphocyte transduction gene loci (e.g., CD2, CD3, CD4, CD8, CD21, CD25, CD44, and CD45) functionally inactivated. However, essentially any lymphocyte transduction gene can be functionally disrupted according to the methods of the invention, provided that polynucleotide sequences that can be used as homology clamps in a targeting construct can be obtained (e.g., from GenBank database, in literature publications, or by routine cloning and sequencing, etc.). Targeting of lymphocyte transduction genes which encode proteins involved in signal transduction (e.g., antigen recognition) and/or lymphocyte selection is particularly preferred (see, *Fundamental Immunology,* 2nd edition (1989), Paul William E., ed. Raven Press, N.Y., which is incorporated herein by reference). Typically, a lymphocyte transduction gene sequence is used as a basis for producing PCR primers that flank a region that will be used as a homology clamp in a targeting construct. The PCR primers are then used to amplify, by high fidelity PCR amplification (Mattila et al. (1991) *Nucleic Acids Res.* 19: 4967; Eckert, K. A. and Kunkel, T. A. (1991) *PCR Methods and Applications* 1: 17; U.S. Pat. No. 4,683,202, which are incorporated herein by reference), a genomic sequence from a genomic clone library or from a preparation of genomic DNA, preferably from the strain of nonhuman animal that is to be targeted with the targeting construct. The amplified DNA is then used as a homology clamp and/or targeting region. Thus, homology clamps for targeting essentially any lymphocyte transduction gene may be readily produced on the basis of nucleotide sequence information available in the art and/or by routine cloning. General principles regarding the construction of targeting constructs and selection methods are reviewed in Bradley et al. (1992) *Bio/Technology* 10: 534, incorporated herein by reference.

Various lymphocyte transduction genes may be functionally disrupted and, optionally, may be relaced by heterologous lymphocyte transduction transgenes; a list of identified human lymphocyte transduction genes is presented in Table I.

TABLE I

Human CD Designations

| DESIGNATION | RECOGNIZED MEMBRANE COMPONENT |
|---|---|
| CD1a | gp49 |
| CD1b | gp45 |
| CD1c | gp43 |
| CD2 | CD58 (LFA-3) receptor, gp50 |
| CD2R | CD2 epitopes restr. to activ. T |
| CD3 | CD3-complex (5 chains), gp/p 26, 20, 16 |
| CD4 | ClassII/HIV receptor, gp59 |
| CD5 | gp67 |
| CD6 | gp100 |
| CD7 | gp40 |
| CD8 | Class 1 receptor, gp32, αα or αβ dimer |
| CD9 | p24 |
| CD10 | gp100, CALLA |
| CD11a | LFA-1, gp180/95 |
| CD11b | C3bi receptor, gp155/95 |
| CD11c | gp150/95 |
| CDw12 | p90–120 |
| CD13 | gp150 |
| CD14 | gp55 |
| CD15 | 3-FAL, X-hapten |
| CD16 | FcRIII, gp50–65 |
| CDw17 | Lactosylceramide |
| CD18 | β chain to CD11a, b, c |
| CD19 | gp5S |
| CD20 | p37/32 |
| CD21 | C3d/EBV-Rec. (CR2), p140 |
| CD22 | gp135, homology to myelin assoc. gp (MAG) |
| CD23 | FcεRII, gp45–50 |
| CD24 | gp41/38 |
| CD25 | IL-2R βchain, gp55 |
| CD26 | gp120 |
| CD27 | p55 (dimer) |
| CD28 | gp44 |
| CD29 | VLA β-integrin β1-chain, Plt GPIIa |
| CD30 | gp120, Ki-1 |
| CD31 | gp140, Plt, GPIIa |
| CDw32 | FcRII, GP40 |
| CD33 | gp67 |
| CD34 | gp105–120 |
| CD35 | CR1 |
| CD36 | gp90, Plt GPIV |
| CD37 | gp40–52 |
| CD38 | p45 |
| CD39 | gp70–100 |
| CD40 | gp50, homology to NGF receptor |
| CD41 | Plt GPIIb-IIIa complex and GPIIb |
| CD42a | Plt GPIX, gp23 |
| CD42b | Plt GPIb, gp135/25 |
| CD43 | Leukosialin, gp95 |
| CD44 | Pgp-1, gp80–95 |
| CD45 | LCA, T200 |
| CD45RA | restricted T200, gp220 |
| CD45RB | restricted T200 |
| CD45RO | restricted T200, gp180 |
| CD46 | Membrane cofactor protein (MCP), gp66/56 |
| CD47 | gp47–52, N-linked glycan |
| CD48 | gp41, PI-linked |
| CDw49b | VLA-α2 chain, Plt GPIa |
| CDw49d | VLA-α4 chain, gp150 |
| CDw49f | VLA-α6 chain, Plt GPIc |
| CDw50 | gp148/108 |
| CDw51 | VNR-α chain |
| CDw52 | Campath-1, gp21–28 |
| CD53 | gp32–40 |
| CD54 | ICAM-1 |
| CD55 | DAF (decay-accelerating factor) |
| CD56 | gp220/135, NKH1, isoform of N-CAM |
| CD57 | gp110, HNK1 |

TABLE I-continued

Human CD Designations

| DESIGNATION | RECOGNIZED MEMBRANE COMPONENT |
|---|---|
| CD58 | LFA-3, gp40–65 |
| CD59 | gp18–20 |
| CDw60 | NeuAc—NeuAc—Gal— |
| CD61 | Integrin β3-, VNR-β chain, Plt GPIIIa |
| CD62 | GMP-140 (PADGEM), gp140 |
| CD63 | gp53 |
| CD64 | FcRI, gp75 |
| CDw65 | Ceramide-dodecasaccharide 4c |
| CD66 | Phosphoprotein gp180–200 |
| CD67 | P100, PI-linked |
| CD68 | gp110 |
| CD69 | gp32/28, AIM |
| CDw70 | Ki-24 |
| CD72 | gp43/39 |
| CD73 | p69 |
| CD74 | gp41/35/33 |
| CDw75 | P53 |
| CD76 | gp85/67 |
| CD77 | Globotriaosylceramide (Gb3) |
| CDw78 | |

Targeting constructs can be transferred into pluripotent stem cells, such as murine embryonal stem cells, wherein the targeting constructs homologously recombine with a portion of an endogenous lymphocyte transduction gene locus and create mutation(s) (i.e., insertions, deletions, rearrangements, sequence replacements, and/or point mutations) which prevent the functional expression of the endogenous lymphocyte transduction gene.

A preferred method of the invention is to delete, by targeted homologous recombination, essential structural elements of an endogenous lymphocyte transduction gene. For example, a targeting construct can homologously recombine with an endogenous CD4 gene and delete a portion spanning substantially all of one or more of the exons to create an exon-depleted allele, typically by inserting a replacement region lacking the corresponding exon(s). Transgenic animals homozygous for the exon-depleted allele (e.g., by breeding of heterozygotes to each other) produce lymphocytes which are essentially incapable of expressing a functional endogenous CD4 molecule. Similarly, homologous gene targeting can be used, if desired, to functionally disrupt a lymphocyte transduction gene by deleting only a portion of an exon of an endogenous lymphocyte transduction gene.

Targeting constructs can also be used to delete essential regulatory elements of a lymphocyte transduction gene, such as promoters, enhancers, splice sites, polyadenylation sites, and other regulatory sequences, including sequences that occur upstream or downstream of the lymphocyte transduction structural gene but which participate in lymphocyte transduction gene expression. Deletion of regulatory elements is typically accomplished by inserting, by homologous double-crossover recombination, a replacement region lacking the corresponding regulatory element(s).

A alternative preferred method of the invention is to interrupt essential structural and/or regulatory elements of an endogenous lymphocyte transduction gene by targeted insertion of a polynucleotide sequence, and thereby functionally disrupt the endogenous lymphocyte transduction gene. For example, a targeting construct can homologously recombine with an endogenous CD4 gene and insert a nonhomologous sequence, such as a neo expression cassette, into a structural element (e.g., an exon) and/or regulatory element (e.g., enhancer, promoter, splice site, polyadenylation site) to yield a targeted CD4 allele having an insertional interruption. The inserted sequence can range in size from about 1 nucleotide (e.g., to produce a frameshift in an exon sequence) to several kilobases or more, as limited by efficiency of homologous gene targeting with targeting constructs having a long nonhomologous replacement region.

Targeting constructs of the invention can also be employed to replace a portion of an endogenous lymphocyte transduction gene with an exogenous sequence (i.e., a portion of a targeting transgene); for example, the first exon of a lymphocyte transduction gene may be replaced with a substantially identical portion that contains a nonsense or missense mutation.

Inactivation of an endogenous mouse lymphocyte transduction locus is achieved by targeted disruption of the appropriate gene by homologous recombination in mouse embryonic stem cells. For inactivation, any targeting construct that produces a genetic alteration in the target lymphocyte transduction gene locus resulting in the prevention of effective expression of a functional gene product of that locus may be employed. If only regulatory elements are targeted, some low-level expression of the targeted gene may occur (i.e., the targeted allele is "leaky"), however the level of expression may be sufficiently low that the leaky targeted allele is functionally disrupted.

Generation of Null Lymphocyte Transduction Alleles and Knockout Mice

In one embodiment of the invention, an endogenous lymphocyte transduction gene in a nonhuman host is functionally disrupted by homologous recombination with a targeting construct that does not comprise a cognate heterologous lymphocyte transduction gene segment. In this embodiment, a portion of the targeting construct integrates into an essential structural or regulatory element of the endogenous lymphocyte transduction gene locus, thereby functionally disrupting it to generate a null allele. Typically, null alleles are produced by integrating a nonhomologous sequence encoding a selectable marker (e.g., a neo gene expression cassette) into an essential structural and/or regulatory sequence of a lymphocyte transduction gene by homologous recombination of the targeting construct homology clamps with endogenous lymphocyte transduction gene sequences, although other strategies (see, infra) may be employed.

Most usually, a targeting construct is transferred by electroporation or microinjection into a totipotent embryonal stem (ES) cell line, such as the murine AB-1 or CCE lines. The targeting construct homologously recombines with endogenous sequences in or flanking a lymphocyte transduction gene locus and functionally disrupts at least one allele of the lymphocyte transduction gene. Typically, homologous recombination of the targeting construct with endogenous lymphocyte transduction locus sequences results in integration of a nonhomologous sequence encoding and expressing a selectable marker, such as neo, usually in the form of a positive selection cassette (infra). The functionally disrupted allele is termed a lymphocyte transduction null allele. ES cells having at least one lymphocyte transduction null allele are selected for by propagating the cells in a medium that permits the preferential propagation of cells expressing the selectable marker. Selected ES cells are examined by PCR analysis and/or Southern blot analysis to verify the presence of a correctly targeted lymphocyte transduction allele. Breeding of nonhuman animals which are heterozygous for a null allele may be performed to produce nonhuman animals homozygous for said null allele, so-called "knockout" animals (Donehower et al. (1992) *Nature* 256: 215; *Science* 26: 1392, incorporated herein by reference). Alternatively, ES cells homozygous for a null allele having an integrated selectable marker can be produced in culture by selection in a medium containing high levels of the selection agent (e.g., G418 or hygromycin). Heterozygosity and/or homozygosity for a correctly targeted null allele can be verified with PCR analysis and/or Southern blot analysis of DNA isolated from an aliquot of a selected ES cell clone and/or from tail biopsies.

If desired, a transgene encoding a cognate heterologous lymphocyte transduction protein can be transferred into a nonhuman host having a lymphocyte transduction null allele, preferably into a nonhuman ES cell that is homozygous for the cognate lymphocyte transduction null allele. It is generally advantageous that the trangene comprises a promoter and enhancer which drive expression of structural sequences encoding a functional heterologous lymphocyte transduction gene product. Thus, for example and not limitation, a knockout mouse homozygous for null alleles at the CD4 locus is preferably a host for a transgene which encodes and expresses a functional human CD4 protein. Lymphocyte transduction transgenes comprise heterologous lymphocyte transduction structural sequences, either in the form of exons having splice junction sequences, as a contiguous coding segment (e.g., a cDNA), or as a combination of these. Most usually, lymphocyte transduction transgenes encode full-length lymphocyte transduction polypeptides, although transgenes can encode truncated lymphocyte transduction molecules, chimeric lymphocyte transduction molecules, and/or amino-substituted lymphocyte transduction variants (i.e., muteins). Typically, transgenes also comprise regulatory elements, such as a promoter and, for optimal expression, an enhancer. It is preferable that a lymphocyte transduction transgene comprises regulatory elements which are naturally associated with the lymphocyte transduction gene that is the source of the structural sequences, and it is usually most preferred that enhancers, if present, are derived from the nonhuman host species. For example and not limitation, a transgene can comprise structural sequences encoding a human CD4 protein, a human CD4 promoter, and a murine CD4 enhancer, arranged in polynucleotide linkage so that the murine CD4 enhancer drives transcription of the human CD4 structural sequences from the human CD4 promoter in a developmentally regulated pattern similar to that of a naturally-occurring murine CD4 gene. Alternatively, a heterologous CD4 transgene can be targeted, by homologous sequence targeting, to a specific site in the host genome having an endogenous regulatory element. For example and not limitation, a transgene comprising a human CD4 promoter and human CD4 structural sequences can be targeted to within several kilobases of the endogenous mouse CD4 enhancer so that the mouse CD4 enhancer exhibits transcriptional control over the human CD4 promoter of the integrated transgene.

Homologous Lymphocyte Transduction Gene Replacement

In an alternative variation of the invention, an endogenous lymphocyte transduction gene in a nonhuman host is functionally disrupted by homologous integration of a cognate heterologous lymphocyte transduction gene, such that the cognate heterologous lymphocyte transduction gene substantially replaces the endogenous lymphocyte transduction gene. Preferably, the heterlogous lymphocyte transduction gene is linked, as a consequence of homologous integration, to regulatory sequences (e.g., an enhancer) of the endogenous lymphocyte transduction gene so that the heterologous lymphocyte transduction gene is expressed under the transcriptional control of regulatory elements from the endogenous lymphocyte transduction gene locus. Nonhuman hosts which are homozygous for such replacement alleles (i.e., a host chromosomal lymphocyte transduction locus which encodes a cognate heterologous lymphocyte transduction gene product) may be produced according to methods described herein. Such homozygous nonhuman hosts generally will express a heterologous lymphocyte transduction protein but do not express the cognate endogenous lymphocyte transduction protein. Most usually, the expression pattern of the heterologous lymphocyte transduction gene will substantially mimic the expression pattern of the cognate endogenous lymphocyte transduction gene in the naturally-occurring nonhuman host. For example but not limitation,sa transgenic mouse having human CD4 gene sequences replacing the endogenous CD4 murine gene sequences and which are transcriptionally controlled by endogenous murine regulatory sequences generally will be expressed similarly to the murine CD4 in naturally occurring nontransgenic mice (e.g., in helper T cells of normal mice).

Generally, a replacement-type targeting construct is employed for homologous gene replacement. Double-crossover homologous recombination between endogenous lymphocyte transduction gene sequences and homology clamps flanking the replacement region (i.e., the heterologous lymphocyte transduction encoding region) of the targeting construct result in targeted integration of the heterologous lymphocyte transduction gene segments. Usually, the homology clamps of the transgene comprise sequences which flank the endogenous lymphocyte transduction gene segments, so that homologous recombination results in concomitant deletion of the endogenous lymphocyte transduction gene segments and homologous integration of the heterologous gene segments. Substantially an entire endogenous lymphocyte transduction gene may be replaced with a heterologous lymphocyte transduction gene by a single targeting event or by multiple targeting events (e.g., sequential replacement of individual exons). One or more selectable markers, usually in the form of positive or negative selection expression cassettes, may be positioned in the targeting construct replacement region; it is usually preferred that selectable markers are located in intron regions of the heterologous replacement region.

ES cells harboring a heterologous lymphocyte transduction gene, such as a replacement allele, may be selected in several ways. First, a selectable marker (e.g., neo, gpt, tk) may be linked to the heterologous lymphocyte transduction gene (e.g., in an intron or flanking sequence) in the targeting construct so that cells having a replacement allele may be selected for. Most usually, a heterologous lymphocyte transduction gene targeting construct will comprise both a positive selection expression cassette and a negative selection expression cassette, so that homologously targeted cells can be selected for with a positive-negative selection scheme. (Mansour et al. (1988) op.cit., incorporated herein by reference). Generally, a positive selection expression cassette is positioned in an intron region of the heterologous lymphocyte transduction gene replacement region, while a negative selection expression cassette is positioned distal to a homology clamp, such that double-crossover homologous recombination will result in the integration of the positive selection cassette and the loss of the negative selection cassette.

Targeting Constructs

Several gene targeting techniques have been described, including but not limited to: co-electroporation, "hit-and-run", single-crossover integration, and double-crossover recombination (Bradley et al. (1992) *Bio/Technology* 10: 534, incorporated herein by reference). The invention can be practiced using essentially any applicable homologous gene targeting strategy known in the art. The configuration of a targeting construct depends upon the specific targeting technique chosen. For example, a targeting construct for single-crossover integration or "hit-and-run" targeting need only have a single homology clamp linked to the targeting region, whereas a double-crossover replacement-type targeting construct requires two homology clamps, one flanking each side of the replacement region.

For example and not limitation, a preferred embodiment is a targeting construct comprising, in order: (1) a first homology clamp having a sequence substantially identical to a sequence within about 3 kilobases upstream (i.e., in the direction opposite to the translational reading frame of the lymphocyte transduction gene exons) of an exon of an endogenous lymphocyte transduction gene, (2) a replacement region comprising a positive selection cassette having a pgk promoter driving transcription of a neo gene, (3) a second homology clamp having a sequence substantially identical to a sequence within about 3 kilobases downstream of said exon of said endogenous lymphocyte transduction gene, and (4) a negative selection cassette, comprising a HSV tk promoter driving transcription of an HSV tk gene. Such a targeting construct is suitable for double-crossover replacement recombination which deletes a portion of the endogenous lymphocyte transduction locus spanning said exon and replaces it with the replacement region having the positive selection cassette. If the deleted exon is essential for expression of a functional lymphocyte transduction gene product, the resultant exon-depleted allele is functionally disrupted and is termed a null allele.

Targeting constructs of the invention comprise at least one homology clamp linked in polynucleotide linkage (i.e., by phosphodiester bonds) to a targeting region. A homology clamp has a sequence which substantially corresponds to, or is substantially complementary to, a predetermined endogenous lymphocyte transduction gene sequence of a nonhuman host animal, and may comprise sequences flanking the predetermined lymphocyte transduction gene.

Although no lower or upper size boundaries for recombinogenic homology clamps for gene targeting have been conclusively determined in the art, the best mode for homology clamps is believed to be in the range between about 50 basepairs and several tens of kilobases. Consequently, targeting constructs are generally at least about 50 to 100 nucleotides long, preferably at least about 250 to 500 nucleotides long, more preferably at least about 1000 to 2000 nucleotides long, or longer. Construct homology regions (homology clamps) are generally at least about 50 to 100 bases long, preferably at least about 100 to 500 bases long, and more preferably at least about 750 to 2000 bases long. It is believed that homology regions of about 7 to 8 kilobases in length are preferred, with one preferred embodiment having a first homology region of about 7 kilobases flanking one side of a replacement region and a second homology region of about 1 kilobase flanking the other side of said replacement region. The length of homology (i.e., substantial identity) for a homology region may be selected at the discretion of the practitioner on the basis of the sequence composition and complexity of the predetermined endogenous lymphocyte transduction gene target sequence (s) and guidance provided in the art (Hasty et al. (1991) *Mol. Cell. Biol.* 11: 5586; Shulman et al. (1990) *Mol. Cell. Biol.* 10: 4466, which are incorporated herein by reference). Targeting constructs have at least one homology region having a sequence that substantially corresponds to, or is substantially complementary to, a predetermined endogenous lymphocyte transduction gene sequence (e.g., an exon sequence, an enhancer, a promoter, an intronic sequence, or a flanking sequence within about 3–20 kb of a lymphocyte transduction gene), such as a CD4 gene sequence. Such a targeting transgene homology region serves as a template for homologous pairing and recombination with substantially identical endogenous lymphocyte transduction gene sequence(s). In targeting constructs, such homology regions typically flank the replacement region, which is a region of the targeting construct that is to undergo replacement with the targeted endogenous lymphocyte transduction gene sequence (Berinstein et al. (1992) *Mol. Cell. Biol.* 12: 360, which is incorporated herein by reference). Thus, a segment of the targeting construct flanked by homology regions can replace a segment of an endogenous lymphocyte transduction gene sequence by double-crossover homologous recombination. Homology regions and targeting regions are linked together in conventional linear polynucleotide linkage (5' to 3' phosphodiester backbone). Targeting constructs are generally double-stranded DNA molecules, most usually linear.

Without wishing to be bound by any particular theory of homologous recombination or gene conversion, it is believed that in such a double-crossover replacement recombination, a first homologous recombination (e.g., strand exchange, strand pairing, strand scission, strand ligation) between a first targeting construct homology region and a first endogenous lymphocyte transduction gene sequence is accompanied by a second homologous recombination between a second targeting construct homology region and a second endogenous lymphocyte transduction gene sequence, thereby resulting in the portion of the targeting construct that was located between the two homology regions replacing the portion of the endogenous lymphocyte transduction gene that was located between the first and second endogenous lymphocyte transduction gene sequences, as shown schematically in FIG. 1. For this reason, homology regions are generally used in the same orientation (i.e., the upstream direction is the same for each homology region of a transgene to avoid rearrangements). Double-crossover replacement recombination thus can be used to delete a portion of an endogenous lymphocyte transduction gene and concomitantly transfer a nonhomologous portion (e.g., a neo gene expression cassette) into the corresponding chromosomal location. Double-crossover recombination can also be used to add a nonhomologous portion into an endogenous lymphocyte transduction gene without deleting endogenous chromosomal portions. However, double-crossover recombination can also be employed simply to delete a portion of an endogenous gene sequence without transferring a nonhomologous portion into the endogenous lymphocyte transduction gene (see Jasin et al. (1988) *Genes Devel.* 2:1353). Upstream and/or downstream from the nonhomologous portion may be a gene which provides for identification of whether a double-crossover homologous recombination has occurred; such a gene is typically the HSV tk gene which may be used for negative selection.

Typically, targeting constructs of the invention are used for functionally disrupting endogenous lymphocyte transduction genes and comprise at least two homology regions separated by a nonhomologous sequence which contains an expression cassette encoding a selectable marker, such as neo (Smith and Berg (1984) *Cold Spring Harbor Symp. Quant. Biol.* 49: 171; Sedivy and Sharp (1989) *Proc. Natl. Acad. Sci. (U.S.A.)* 86: 227; Thomas and Capecchi (1987) op.cit., which are incorporated herein by reference). However, some targeting transgenes of the invention may have the homology region(s) flanking only one side of a nonhomologous sequence. Targeting transgenes of the invention may also be of the type referred to in the art as "hit-and-run" or "in-and-out" transgenes (Valancius and Smithies,(1991) *Mol. Cell. Biol.* 11: 1402; Donehower et al. (1992) *Nature* 356: 215; (1991) *J. NIH Res.* 3: 59; which are incorporated herein by reference). FIG. 2 schematically portrays an insertion targeting transgene homologously recombining with an endogenous lymphocyte transduction gene sequence (for illustration, an exon, such as a $\mu$ exon) to produce a functionally disrupted lymphocyte transduction gene having an integrated nonhomologous sequence (e.g., neo gene).

The positive selection expression cassette encodes a selectable marker which affords a means for selecting cells which have integrated targeting transgene sequences spanning the positive selection expression cassette. The negative selection expression cassette encodes a selectable marker which affords a means for selecting cells which do not have an integrated copy of the negative selection expression cassette. Thus, by a combination positive-negative selection protocol, it is possible to select cells that have undergone homologous replacement recombination and incorporated the portion of the transgene between the homology regions (i.e., the replacement region) into a chromosomal location by selecting for the presence of the positive marker and for the absence of the negative marker. Selectable markers typically are also be used for hit-and-run targeting constructs and selection schemes (Valancius and Smithies, op.cit., incorporated herein by reference).

An expression cassette typically comprises a promoter which is operational in the targeted host cell (e.g., ES cell) linked to a structural sequence that encodes a protein or polypeptide that confers a selectable phenotype on the targeted host cell, and a polyadenylation signal. A promoter included in an expression cassette may be constitutive, cell type-specific, stage-specific, and/or modulatable (e.g., by hormones such as glucocorticoids; MMTV promoter), but is expressed prior to and/or during selection. An expression cassette can optionally include one or more enhancers, typically linked upstream of the promoter and within about 3–10 kilobases. However, when homologous recombination at the targeted endogenous site(s) places the nonhomologous sequence downstream of a functional endogenous promoter, it may be possible for the targeting construct replacement region to comprise only a structural sequence encoding the selectable marker, and rely upon the endogenous promoter to drive transcription (Doetschman et al. (1988) *Proc. Natl. Acad. Sci. (U.S.A.)* 85: 8583, incorporated herein by reference). Similarly, an endogenous enhancer located near the targeted endogenous site may be relied on to enhance transcription of transgene sequences in enhancerless transgene constructs. Preferred expression cassettes of the invention encode and express a selectable drug resistance marker and/or a HSV thymidine kinase enzyme. Suitable drug resistance genes include, for example: gpt (xanthine-guanine phosphoribosyltransferase), which can be selected for with mycophenolic acid; neo (neomycin phosphotransferase), which can be selected for with G418 or hygromycin; and DFHR (dihydrofolate reductase), which can be selected for with methotrexate (Mulligan and Berg (1981) *Proc. Natl. Acad. Sci. (U.S.A.)* 78: 2072; Southern and Berg (1982) *J. Mol. Appl. Genet.* 1: 327; which are incorporated herein by reference).

Selection for correctly targeted recombinants will generally employ at least positive selection, wherein a nonhomologous expression cassette encodes and expresses a functional protein (e.g., neo or gpt) that confers a selectable phenotype to targeted cells harboring the endogenously integrated expression cassette, so that, by addition of a selection agent (e.g., G418 or mycophenolic acid) such targeted cells have a growth or survival advantage over cells which do not have an integrated expression cassette.

It is preferable that selection for correctly targeted homologous recombinants also employ negative selection, so that cells bearing only nonhomologous integration of the transgene are selected against. Typically, such negative selection employs an expression cassette encoding the herpes simplex virus thymidine kinase gene (HSV tk) positioned in the transgene so that it should integrate only by nonhomologous recombination. Such positioning generally is accomplished by linking the HSV tk expression cassette (or other negative selection cassette) distal to the recombinogenic homology regions so that double-crossover replacement recombination of the homology regions transfers the positive selection expression cassette to a chromosomal location but does not transfer the HSV tk gene (or other negative selection cassette) to a chromosomal location, as represented schematically in FIG. 3. A nucleoside analog, gancyclovir, which is preferentially toxic to cells expressing HSV tk, can be used as the negative selection agent, as it selects for cells which do not have an integrated HSV tk expression cassette. FIAU may also be used as a selective agent to select for cells lacking HSV tk.

In order to reduce the background of cells having incorrectly integrated targeting construct sequences, a combination positive-negative selection scheme is typically used (Mansour et al. (1988) op.cit., incorporated herein by reference). Positive-negative selection involves the use of two active selection cassettes: (1) a positive one (e.g., the neo gene), that can be stably expressed following either random integration or homologous targeting, and (2) a negative one (e.g., the HSV tk gene), that can only be stably expressed following random integration, and cannot be expressed after correctly targeted double-crossover homologous recombination. By combining both positive and negative selection steps, host cells having the correctly targeted homologous recombination between the transgene and the endogenous lymphocyte transduction gene can be obtained.

Generally, targeting constructs of the invention preferably include: (1) a positive selection expression cassette flanked by two homology regions that are substantially identical to host cell endogenous lymphocyte transduction gene sequences, and (2) a distal negative selection expression cassette. However, targeting constructs which include only a positive selection expression cassette can also be used. Typically, a targeting construct will contain a positive selection expression cassette which includes a neo gene linked downstream (i.e., towards the carboxy-terminus of the encoded polypeptide in translational reading frame orientation) of a promoter such as the HSV tk promoter or the pgk promoter. More typically, the targeting transgene will also contain a negative selection expression cassette which includes an HSV tk gene linked downstream of a HSV tk promoter. For example, but not to limit the invention, a schematic representation of a typical positive-negative CD4 targeting construct of the invention is shown in FIG. 4.

It is preferred that targeting constructs of the invention have homology regions that are highly homologous to the predetermined target endogenous DNA sequence(s), preferably isogenic (i.e., identical sequence). Isogenic or nearly isogenic sequences may be obtained by genomic cloning or high-fidelity PCR amplification of genomic DNA from the strain of nonhuman animals which are the source of the ES cells used in the gene targeting procedure. Typically, targeting polynucleotides of the invention have at least one homology region that is at least about 50 nucleotides long, and it is preferable that homology regions are at least about 75 to 100 nucleotides long, and more preferably at least about 200–2000 nucleotides long, although the degree of sequence homology between the homology region and the targeted sequence and the base composition of the targeted sequence will determine the optimal and minimal homology region lengths (e.g., G-C rich sequences are typically more thermodynamically stable and will generally require shorter homology region length). Therefore, both homology region length and the degree of sequence homology can only be determined with reference to a particular predetermined sequence, but homology regions generally must be at least about 50 nucleotides long and must also substantially correspond or be substantially complementary to a predetermined endogenous target sequence. Preferably, a homology region is at least about 100 nucleotides long and is identical to or complementary to a predetermined target sequence in or flanking a lymphocyte transduction gene. If it is desired that correctly targeted homologous recombinants are generated at high efficiency, it is preferable that at least one homology region is isogenic (i.e., has exact sequence identity with the crossover target sequence(s) of the endogenous lymphocyte transduction gene), and is more preferred that isogenic homology regions flank the exogenous targeting construct sequence that is to replace the targeted endogenous lymphocyte transduction sequence.

Generally, any predetermined endogenous lymphocyte transduction locus can be altered by homologous recombination (which includes gene conversion) with an targeting transgene that has at least one homology region which substantially corresponds to or is substantially complementary to a predetermined endogenous lymphocyte transduction gene locus sequence in a mammalian cell having said predetermined endogenous lymphocyte transduction gene sequence. Typically, a targeting transgene comprises a portion having a sequence that is not present in the preselected endogenous targeted lymphocyte transduction sequence(s) (i.e., a nonhomologous portion) which may be as small as a single mismatched nucleotide or may span up to about several kilobases or more of nonhomologous sequence. Generally, such nonhomologous portions are flanked on each side by homology regions, although a single flanking homology region may be used (e.g., in insertion transgenes). Nonhomologous portions are used to make insertions, deletions, and/or replacements in a predetermined endogenous targeted lymphocyte transduction gene sequence, and/or to make single or multiple nucleotide substitutions in a predetermined endogenous target DNA sequence so that the resultant recombined sequence (i.e., a functionally disrupted endogenous lymphocyte transduction gene) incorporates the sequence information of the nonhomologous portion of the targeting construct(s). Substitutions, additions, and deletions may be as small as 1 nucleotide or may range up to about 2 to 10 kilobases or more. A preferred nonhomologous portion of a targeting transgene is a selectable drug resistance marker (e.g., the neo gene), which may be transferred to a chromosomal location, stably replicated, and selected for with a selection agent (e.g., G418). Targeting transgenes can be used to inactivate one or more lymphocyte transduction genes in a cell, such as in a murine ES cell, and transgenic nonhuman animals harboring such inactivated genes may be produced.

Once the specific lymphocyte transduction gene(s) to be modified are selected, their sequences will be scanned for possible disruption sites (e.g., a segment of the murine CD4 gene spanning the second and third exons). Plasmids are engineered to contain an appropriately sized construct replacement sequence with a deletion or insertion in the lymphocyte transduction gene of interest and at least one flanking homology region which substantially corresponds or is substantially complementary to an endogenous target DNA sequence. Typically two flanking homology regions are used, one on each side of the replacement region sequence. For example, but not to limit the invention, one homology region may be substantially identical to a sequence upstream (i.e., the direction towards the transcription start site(s) of the murine CD4 second exon and a second homology region may be substantially identical to a sequence downstream of the murine CD4 third exon.

A preferred method of the invention is to transfer a targeting transgene into a pluripotent stem cell line which can be used to generate transgenic nonhuman animals following injection into a host blastocyst. A particularly preferred embodiment of the invention is a CD4 gene targeting construct containing both positive (e.g., neo) and, optionally, negative (e.g., HSV tk) selection expression cassettes. The CD4 targeting transgene is transferred into mouse ES cells (e.g., by electroporation) under conditions suitable for the continued viability of the electroporated ES cells. The electroporated ES cells are cultured under selective conditions for positive selection (e.g., a selective concentration of G418), and optionally are cultured under selective conditions for negative selection (e.g., a selective concentration of gancyclovir or FIAU), either simultaneously or sequentially. Selected cells are then verified as having the correctly targeted transgene recombination by PCR analysis according to standard PCR or Southern blotting methods known in the art (U.S. Pat. No. 4,683,202; Erlich et al., (1991) *Science* 252: 1643, which are incorporated herein by reference). Correctly targeted ES cells are then transferred into suitable blastocyst hosts for generation of chimeric transgenic animals according to methods known in the art (Capecchi, M. (1989) op.cit., incorporated herein by reference).

Briefly, the invention involves the inactivation of an lymphocyte transduction gene, most usually a CD4 gene, by homologous recombination in a pluripotent cell line that is capable of differentiating into germ cell tissue. A DNA construct that contains an altered, copy of a mouse lymphocyte transduction gene (e.g., a CD4 gene) is introduced into the nuclei of embryonic stem cells. In a portion of the cells, the introduced DNA recombines with the endogenous copy of the mouse gene, replacing it with the altered copy. Cells containing the newly engineered genetic lesion are injected into a host mouse embryo, which is reimplanted into a recipient female. Some of these embryos develop into chimeric mice that possess germ cells derived from the mutant cell line. Therefore, by breeding the chimeric mice it is possible to obtain a new line of mice containing the introduced genetic lesion (reviewed by Capecchi, M. (1989) op.cit.).

To disrupt the murine CD4 gene, a targeting construct based on the design employed by Jaenisch and co-workers (Zjilstra, et al. (1989) op.cit.) for the successful disruption of the mouse $\beta$2-microglobulin gene can be used. The neomycin resistance gene (neo), from the plasmid pMCINEO is inserted into the coding region of the target CD4 gene. The pMCIneo insert uses a hybrid viral promoter/enhancer sequence to drive neo expression. This promoter is active in embryonic stem cells. Therefore, neo can be used as a selectable marker for integration of the knock-out construct. The HSV thymidine kinase (tk) gene is added to the end of the construct as a negative selection marker against random insertion events (Zjilstra, et al., op.cit.).

Vectors containing a targeting construct are typically grown in E. coli and then isolated using standard molecular biology methods, or may be synthesized as oligonucleotides. Direct targeted inactivation which does not require prokaryotic or eukaryotic vectors may also be done. Targeting transgenes can be transferred to host cells by any suitable technique, including microinjection, electroporation, lipofection, biolistics, calcium phosphate precipitation, and viral-based vectors, among others. Other methods used to transform mammalian cells include the use of Polybrene, protoplast fusion, and others (see, generally, Sambrook et al. Molecular Cloning: A Laboratory Manual, 2d ed., 1989, Cold Spring Harbor Laboratory Press, Cold Spring Harbor, N.Y., which is incorporated herein by reference).

It is preferable to use a transfection technique with linearized transgenes containing only modified target gene sequence(s) and without vector sequences. The modified gene site is such that a homologous recombinant between the exogenous targeting construct and the endogenous DNA target sequence can be identified by using carefully chosen primers and PCR or by Southern blot analysis, followed by analysis to detect if PCR products or Southern blot bands specific to the desired targeted event are present (Erlich et al., (1991) op.cit.), which is incorporated herein by reference). Several studies have already used PCR to successfully identify the desired transfected cell lines (Zimmer and Gruss (1989) Nature 338: 150; Mouellic et al. (1990) Proc. Natl. Acad. Sci. (U.S.A.) 87: 4712; Shesely et al. (1991) Proc. Natl. Acad. Sci. USA 88: 4294, which are incorporated herein by reference). This approach is very effective when the number of cells receiving exogenous targeting transgene(s) is high (i.e., with electroporation or with liposomes) and the treated cell populations are allowed to expand (Capecchi, M. (1989) op.cit., incorporated herein by reference).

For making transgenic non-human animals (which include homologously targeted non-human animals), embryonal stem cells (ES cells) are preferred. Murine ES cells, such as AB-1 line grown on mitotically inactive SNL76/7 cell feeder layers (McMahon and Bradley, Cell 62:1073–1085 (1990)) essentially as described (Robertson, E. J. (1987) in Teratocarcinomas and Embryonic Stem Cells: A Practical Approach. E. J. Robertson, ed. (Oxford: IRL Press), p. 71–112) may be used for homologous gene targeting. Other suitable ES lines include, but are not limited to, the E14 line (Hooper et al. (1987) Nature 326: 292–295), the D3 line (Doetschman et al. (1985) J. Embryol. Exp. Morph. 87: 27–45), and the CCE line (Robertson et al. (1986) Nature 323: 445–448). The success of generating a mouse line from ES cells bearing a specific targeted mutation depends on the pluripotence of the ES cells (i.e., their ability, once injected into a host blastocyst, to participate in embryogenesis and contribute to the germ cells of the resulting animal). The blastocysts containing the injected ES cells are allowed to develop in the uteri of pseudopregnant nonhuman females and are born as chimeric mice. The resultant transgenic mice are chimeric for cells having inactivated endogenous lymphocyte transduction loci and are backcrossed and screened for the presence of the correctly targeted transgene(s) by PCR or Southern blot analysis on tail biopsy DNA of offspring so as to identify transgenic mice heterozygous for the inactivated lymphocyte transduction locus/loci. By performing the appropriate crosses, it is possible to produce a transgenic nonhuman animal homozygous for multiple functionally disrupted lymphocyte transduction loci, and optionally also for a transgene encoding a heterologous lymphocyte transduction protein. Such transgenic animals are substantially incapable of making an endogenous lymphocyte transduction gene product. For these reasons, such transgenic animals are satisfactory hosts for introduction of transgenes encoding cognate heterologous lymphocyte transduction proteins, such as, for example, a transgene encoding human CD4.

Transgenes Encoding Heterologous Lymphocyte Transduction Proteins

Having described the production of nonhuman animals with functionally disrupted endogenous lymphocyte transduction genes, reconstitution of the "knockout" animals with transgenes encoding the cognate heterologous lymphocyte transduction molecules is provided. By combining a lymphocyte transduction gene "knockout" with expression of the cognate heterologous lymphocyte transduction gene, it is possible to generate nonhuman animals having lymphocytes which express a xenogeneic lymphocyte transduction molecule in place of the naturally-occurring nonhuman lymphocyte transduction molecule. Such nonhuman animals are well-suited for studying the function of xenogeneic lymphocyte transduction molecules (e.g., human CD4) in a in vivo nonhuman system which can be experimentally manipulated. For example, mice homozygous for functional disruption of the endogenous CD4 locus and expressing heterologous human CD4 in an expression pattern similar to naturally-occurring murine CD4 have various applications, including but not limited to: (1) serving as in vivo models for HIV attachment and pathogenesis, (2) serving as i vivo models for MHC class II-mediated human autoimmune diseases, (3) providing a system for studying human diseases that involve $CD4^+$ T cells, and (4) screening for drugs which interact with the human CD4 glycoprotein, among others. For example, CD4 knockout mice expressing a human CD4 transgene would be useful for screening for therapeutic or prophylactic agents that inhibit the human CD4-mediated pathogenesis of HIV virions.

In a preferred embodiment of the invention, a transgene encoding a heterologous lymphocyte transduction protein is transferred into an ES cell to produce a transgenic nonhuman animal lacking expression of an endogenous lymphocyte transduction gene (such as murine CD4) and having developmentally regulated expression of the cognate heterologous lymphocyte transduction gene (such as human CD4). A transgene encoding a heterologous lymphocyte transduction protein comprises structural sequences encoding a heterologous lymphocyte transduction protein, and generally also comprises linked regulatory elements that drive expression of the heterologous lymphocyte transduction protein in the nonhuman host. However, endogenous regulatory elements in the genome of the nonhuman host may be exploited by integrating the transgene sequences into a chromosomal location containing functional endogenous regulatory elements which are suitable for the expression of the heterologous structural sequences. Such targeted integration is usually performed by homologous gene targeting as described supra, wherein the heterologous transgene would comprise at least one homology clamp.

When a heterologous transgene relies on its own regulatory elements, suitable transcription elements and polyadenylation sequence(s) are included. At least one promoter is linked upstream of the first structural sequence in an orientation to drive transcription of the heterologous structural sequences. Usually the promoter from the naturally-occurring heterologous gene is used (e.g., a human CD4 promoter is used to drive expression of a human CD4 transgene), alternatively, the promoter from the endogenous cognate lymphocyte transduction gene may be used (e.g., the murine CD4 promoter is used to drive expression of a human CD4 transgene). Various promoters having different strengths (e.g., pgk, tk, dhfr) may be substituted in the discretion of the practitioner, however it is essential that the promoter function in the nonhuman host and it is desirable that the promoter drive expression in a developmental pattern (and at levels) similar to the naturally-occurring cognate endogenous lymphocyte transduction gene. Likewise, it is usually preferred that an enhancer is included in a heterologous transgene, typically an enhancer from the cognate lymphocyte transduction gene of the nonhuman host or, less preferably, the enhancer from the heterologous gene. For example, a heterologous CD4 transgene can employ murine CD4 enhancer linked upstream of human CD4 structural sequences transcribed by the human CD4 promoter. Other combinations may also be employed, but it is believed that in the best mode of the invention an enhancer from the cognate lymphocyte transduction gene of the nonhuman host should be employed to control transcription of the heterologous lymphocyte transduction gene sequences if expression similar to that of the naturally-occurring lymphocyte transduction gene of the nonhuman host is desired. In one embodiment, the human CD4 promoter and murine CD4 enhancer are employed to drive transcription of essentially any human lymphocyte transduction gene, albeit in a CD4 expression pattern.

A heterologous transgene generally encodes a full-length lymphocyte transduction protein. The heterologous transgene may comprise a polynucleotide spanning the entire genomic lymphocyte transduction gene or portion thereof, may comprise a minigene, may comprise a single contiguous coding segment (e.g., cDNA), or may comprise a combination thereof. The following examples are provided for illustration of the breadth of the invention and not for limitation. A human CD4 transgene may comprise a full-length human CD4 cDNA (GenBank: Humatct4a) linked to the human CD4 promoter and murine CD4 enhancer. Also for example, a human CD2 transgene may comprise a full-length human CD2 cDNA (GenBank: Humantcd2, Humcd2a, Humatccd2) linked to a human CD2 promoter and murine enhancer. A human CD21 transgene may comprise a full-length human CD21 cDNA (GenBank: Humebvr) linked to a human CD21 promoter and murine enhancer. A human CD2 transgene may comprise a minigene which comprises the human CD2 gene exons in order (GenBank: Humcd21, Humcd22, Humcd23, Humcd24, Humcd25, also Humcd2r1, Humcd2r2, Humcd2r3, Humcd2r4), the human CD2 promoter upstream of the first exon, and a murine enhancer upstream of the promoter. A human CD21 transgene may comprise a minigene which comprises the human CD21 exons in order (GenBank: Humbur02, Humbur03, Humbur04, Humbur05, Humbur06, Humbur07, Humbur08, Humbur09, Humbur10, Humbur11, Humbur12, Humbur13, Humbur 14), the upstream flanking sequence of the human CD21 gene (GenBank: Humbur01) positioned upstream of the first exon, and, optionally, a murine enhancer upstream of the promoter. A human CD44 minigene may comprise a human CD44 cDNA (GenBank: Humcd44b, Humcd44e, Humcd44er; Jackson et al. (1992) op.cit., incorporated herein by reference), or may comprise a minigene constructed out of CD44 gene exons (GenBank: Humcd44a, Humcd44f, Humcd44g, Humcd44h, Humcd44i, Humcd44j) to encode one or more of the alternatively spliced CD44 variant proteins (Jackson et al. (1992) op.cit., incorporated herein by reference).

Transgenes encoding heterologous lymphocyte transduction molecules may be transferred into the nonhuman host genome in several ways. A heterologous transgene may be targeted to a specific predetermined chromosomal location by homologous targeting, as described supra for gene targeting. Large (i.e., larger than about 50 kb) heterologous transgenes may be transferred into a host genome in pieces, by sequential homologous targeting, to reconstitute a complete heterologous gene in an endogenous host chromosomal location. In contradistinction, a heterologous transgene may be randomly integrated separately from a lymphocyte transduction gene targeting construct. A heterologous transgene may be co-transferred with a lymphocyte transduction gene targeting construct and, if desired, selected for with a separate, distinguishable selectable marker and/or screened with PCR or Southern blot analysis of selected cells. Alternatively, a heterologous trangene may be introduced into ES cells prior to or subsequent to introduction of a lymphocyte transduction gene targeting construct and selection therefor. Most conveniently, a heterologous transgene is introduced into the germline of a nonhuman animal by nonhomologous transgene integration via pronuclear injection, and resultant transgenic lines are bred into a homozygous knockout background having functionally disrupted cognate endogenous lymphocyte transduction gene. Homozygous knockout mice can also be bred and the heterologous transgene introduced into embryos of knockout mice directly by standard pronuclear injection.

Although the present invention has been described in some detail by way of illustration for purposes of clarity of understanding, it will be apparent that certain changes and modifications may be practiced within the scope of the claims.

EXPERIMENTAL EXAMPLES

Example 1

Inactivation of the Murine CD4 Gene by Homologous Gene Targeting

As a prelude to transgenic reconstitution experiments, the murine CD4 gene was inactivated by homologous recombination in embryonic stem cells using the strategy depicted schematically in FIG. 5. The targeting construct was made from cosmid clones isolated from a mouse genomic library available from Dr. Glenn Evans, Salk Institute, La Jolla, Calif. The isolation of the cosmid clones containing the murine CD4 gene was accomplished by screening the library with a murine CD4 cDNA probe, and has be described previously (Sawada, S. and Littman, D. R. (1991) *Mol. Cell. Biol.* 11: 5506, incorporated herein by reference). A 0.8 kb EcoRI-KpnI fragment spanning exon IV and part of exon V of the murine CD4 gene was isolated and subcloned in the prokaryotic vector pBS (Stratagene, San Diego, Calif.).

The plasmid pMC1neo (Zjilstra et al. (1989) op.cit.) is digested with XhoI and HindIII and the XhoI-HindIII insert containing the neo expression cassette (neo gene linked to the HSV tk promoter and polyoma enhancer) is isolated after agarose gel electrophoresis and repaired with Klenow fragment to generate blunt ends. This fragment containing the positive selection expression cassette is inserted into the T4 polymerase-blunt-ended KpnI site of exon V of the murine CD4 gene fragment cloned in pBS (FIG. 5). This insertion disrupts the coding sequence of the second Ig-like domain of CD4. A blunt-ended 4.0 kb KpnI-BamHI fragment of the murine CD4 cosmid clone was then ligated into the blunt-ended BamHI site at the end of the neo cassette in order to provide sequence homology on the.3' end (downstream) of the disruption. A blunt-ended 6.5 kb NotI-BamHI fragment containing the disrupted sequence was then ligated into the blunt-ended HindIII site of a vector containing two copies of the 2.0 kb MC1-TK negative selection cassette (Mansour et al. (1988) op.cit., incorporated herein by reference); MC1-TK is the HSV-tk gene and promoter linked to two polyoma enhancers. The final construct had murine CD4 genomic sequence disrupted by a neo resistance gene and flanked on both sides by the MC1-TK segment. The resultant plasmid was cloned, grown up, and isolated in large-scale culture and linearized at the ClaI site. Approximately 20 million murine ES cells (D3) were electroporated with about 20 μg of linearized plasmid. The electroporated cells were positively selected with G418 (150–200 μg/ml) and about 1,000–5,000 individual clones were obtained. In pilot experiments, negative selection was found to be ineffective and so was not used thereafter, although in other circumstances negative selection may be desirable. PCR was used to screen pools of 10–30 colonies for homologous recombination at the CD4 locus, and then individual colonies were rescreened by PCR and verified by Southern blotting. Correctly-targeted homologous recombinants were frozen down according to conventional methods.

PCR analysis can be performed using various combinations of PCR primers. In general, a first PCR primer hybridizes to a neo sequence (e.g., 5'-CTT GTT CAA TGG CCG ATC CCA-3' or 5'-TTC TTG ACG AGT TCT GAG GGG ATC GGC-3') and a reverse PCR primer hybridizes to an endogenous murine CD4 sequence downstream or upstream of the targeting construct homology regions (e.g., 5'-TAG TTC TGA ATG GTC ATT AA-3').

Frozen stocks of the pooled clones having the targeted, functionally disrupted CD4 gene are thawed under suitable conditions, cultured under selection conditions, and subcloned according to standard methods known in the art. Each individual clone is grown separately. Half of the cells derived from each clone are then frozen and the other half are used for PCR analysis. Those clones which are positive for correct transgene targeting as shown by PCR and/or Southern blot analysis are microinjected into C57Bl/6J blastocysts as described (Bradley, A. (1987) in *Teratocarcinomas and Embryonic Stem Cells: A Practical Approach*. E. J. Robertson, ed. (Oxford: IRL Press), p. 113–151) and transferred into the uteri of pseudopregnant females to generate chimeric mice representing a mixture of cells derived from the input ES cells and the host blastocyst. The offspring were analyzed for the presence of a functionally disrupted CD4 gene by taking a tail biopsy and performing Southern blot analysis of a BglII digest using a probe spanning murine CD4 exons II–IX (see, FIG. 5). The probe detected a 1.2 kb insertion event corresponding to the expected insertion of the pMC1neo cassette into exon V of the murine CD4 gene (FIG. 8). Other probes were used to confirm correct gene targeting of the CD4 gene. Southern blot analysis was used to determine whether chimeric offspring harbor the disrupted exon V allele, and thus whether the transgene has been correctly targeted.

Transgenic mice having correctly targeted homologous recombinations were backcrossed and Southern blot analysis was used to demonstrate germline transmission of the functionally disrupted murine CD4 allele. Mice bearing a functionally disrupted murine CD4 allele are bred to generate mice which are homozygous for an inactivated heavy chain gene. Mice which were homozygous for the disrupted allele lacked surface expression of murine CD4 on both thymocytes and T cells (FIGS. X2 and X3). Approximately 90 percent of peripheral αβ T cells were CD8$^+$. A significant consequence of the knockout was the loss of helper T cell activity and other MHC class II-restricted T cell responses. Antibody titres were reduced at least ten-fold following immunization with foreign antigens, and the T cells in these mice fail to proliferate when exposed to foreign MHC class II molecules, despite normal MHC class I responses.

CD4 knockout mice harboring human CD4 transgene(s) are bred with other knockout genotypes, particularly with MHC class II gene knockout mice having human MHC class II transgene(s), to generate mice having multiple endogenous knockout loci reconstituted with the cognate human transgene. Such mice are used for vaccine development and to study viral pathogenesis in animal models having human lymphocyte cell surface proteins.

Example 2

Rescue of CD4 Expression with a Human CD4 Transgene

Previous attempts by others to achieve appropriate expression of CD4 transgenes in mice have not been successful. Use of heterologous T cell-specific enhancers and promoters has resulted in the expression of CD4 in thymocytes and in T cells which do not normally express this protein, such as mature CD8$^+$ cells, as well as inappropriate levels of CD4 expression.

Figure 9:
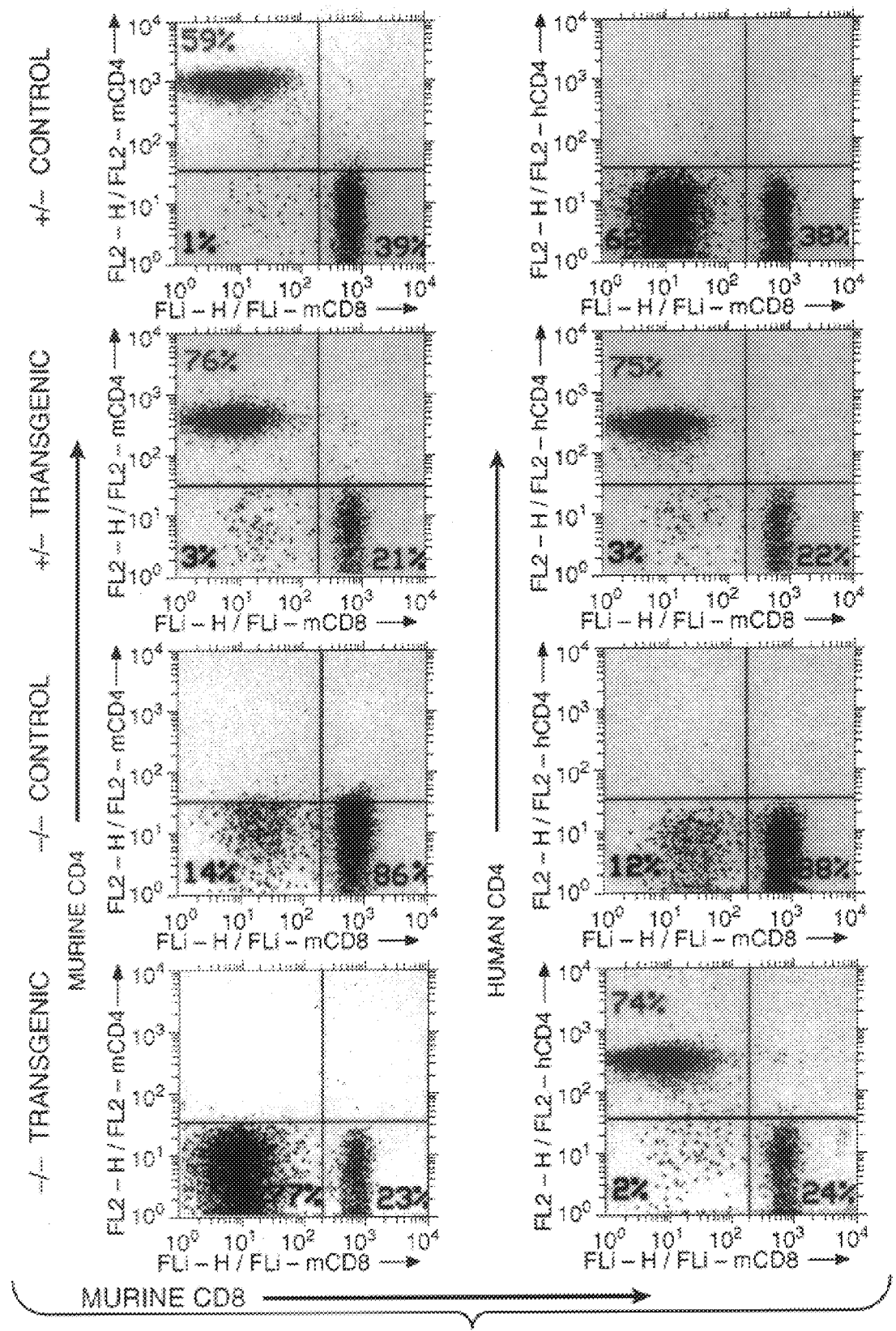
FIG. 9 is a flow cytometric analysis of peripheral T lymphocytes from mice heterozygous for CD4 knockout (+/–) or homozygous for knockout (–/–) and either harboring a human CD4 minigene transgene (Transgenic) or nor harboring a human transgene (Control).

A T-cell specific enhancer element located about 13 kb upstream of the transcription initiation site in the murine CD4 gene was isolated (Sawada, S. and Littman, D. R. (1991) op.cit., incorporated herein by reference) and the sequence spanning this enhancer is provided in FIG. 6 (GenBank: Muscd4en). A 4.5 kb BglII-EcoRI fragment encompassing this enhancer was ligated upstream of a human CD4 minigene which includes the promoter and all of the protein coding region of the human CD4 gene (see, FIG. 7). The human minigene was constructed as follows. A human liver genomic DNA library in a lambda cloning vector (Maniatis library) was screened by probing with full-length cDNA to the human CD4 mRNA using standard hybridization methods (e.g., Benton-Davis screening). Clones λHG1 and λHG6 were obtained and each had EcoRI inserts of approximately 15–16 kb. λHG1 contained exons 1 through 3 of the human CD4 gene and also contained about 3 kb of the 5' upstream flanking sequence. λHG6 contained exons 4 through 10 of the human CD4 gene and also contained about 8 kb of sequence downstream from the polyadenylation site. The EcoRI inserts were isolated and ligated head-to-tail (i.e., in germline configuration with exons 1–3 followed, in order, by exons 4–10 in correct orientation to encode a functional CD4 protein) in a plasmid cloning vector (FIG. 7). The CD4 enhancer was ligated upstream of the head-to-tail ligation product in a polylinker region of the plasmid cloning vector. The resultant construct was cloned and the human CD4 minigene construct was cut out by digestion with NotI. Vector sequences were deleted from the minigene and transgenic mice were created by standard pronuclear injection of murine embryos. Of three transgenic founders, two expressed significant levels of human CD4 on the surface of a subset of their peripheral T cells as determined by flow cytometry. One of these mice, #2362, carried approximately six copies of the transgene and expressed a level of human CD4 equivalent to that seen on peripheral human CD4$^+$ T cells (FIG. 9). The other founder mouse, #2354, carried approximately 30 copies of the transgene and expressed about 3-fold more human CD4 per cell. Both transgenic founders and their offspring lacked human CD4 on their peripheral CD8$^+$ T lymphocytes (FIG. 9), consistent with appropriate transcriptional silencing of the human CD4 transgene.

The male transgenic founder #2362 was backcrossed into the murine CD4-knockout background. This was achieved in a single generation, because one of the founder's parents had been a CD4−/− male. Crosses between male 2362 and CD4−/− females yielded equal numbers of mice displaying the four distinct phenotypes shown in the flow cytometric analysis in FIG. 9. Mice homozygous for the CD4 gene disruption have few CD8⁻ thymocytes or CD8⁻ peripheral T cells compared to CD4+/− controls. In transgenic mice, human CD4 is expressed on these CD8⁻ cells and restores their numbers to approximately the levels seen in the presence of mouse CD4. Like thymocytes from normal mice, those from the transgenic mice can be subdivided into mature and immature subpopulations based on expression of CD4(human) and CD8(murine). Similarly, peripheral T cells express either human CD4 or murine CD8, but not both, reflecting appropriate regulation of the human CD4 transgene.

The FACS data of FIG. 9 indicate that expression of human CD4 can rescue a lineage of cells whose development is otherwise prematurely arrested due to the absence of endogenous CD4. To determine whether these cells have the properties of helper T cells that are absent in the CD4−/− mice, their functions were analyzed in two helper cell-dependent experimental systems. To test for MHC class II-specific allogeneic responses, CD4−/− transgenic and control lymphocytes were challenged in vitro with irradiated cells from either B6.H-2$^{bm1}$ or B6.H-2$^{bm12}$ mouse strains. These mice are congenic with C57BL/6 and bear mutations in either the class I K$^b$ or class II-A$^b$ genes, respectively. T cells from control CD4+/− H-2$^b$ mice were tolerant to cells from MHC-syngeneic C57BL/6 mice, but proliferated in response to stimulation with either the bm1 or bm12 mutant haplotype cells. Whereas CD4−/− cells also responded to the class I alloantigen K$^{bm1}$, they did not proliferate when challenged with the class II alloantigen bm12. There was a restoration of a strong bm12 response in CD4−/− mice transgenic for human CD4, showing rescue of class II-restricted responses by the product of the human CD4 transgene, and indicating that human CD4 and murine CD4 are functionally equivalent in their interactions with murine MHC class II.

Due to the absence of CD4+ helper T cells, CD4−/− mice are deficient in generating T cell-dependent antibody responses. To determine whether this defect is corrected by expression of the human CD4 transgene, mice were immunized with the hapten TNP coupled to keyhole limpet hemocyanin (TNP-KLH) and sera samples were collected at days 0, 10, and 14 and assayed for the presence of TNP-specific antibodies using an isotype-specific indirect ELISA. The reduction in antibody titer observed in CD4−/− mice was largely corrected by expression of human CD4 by the transgene. Levels of specific antibodies in the CD4−/− mice bearing the human CD4 transgene were similar to those obtained in the CD4+/− control mice.

Effective signal transduction through the T cell antigen receptor (TCR) involves coordinate engagement of peptide-presenting MHC class I and class II molecules by the TCR and either CD4 or CD8 molecules, respectively. The cytoplasmic tyrosine kinase p56lck, which is associated with the cytoplasmic domains of both CD4 and CD8 is thus brought into the TCR complex and potentiates the TCR-mediated signal. The results provided from this Example demonstrate that the human CD4 molecule can also effectively substitute for the murine CD4 in vivo for both thymocyte development and for peripheral T cell function. Thus, human CD4 can provide appropriate signal transduction functions in mice through the interaction of its external and cytoplasmic domains with murine class II and p56lck molecules, respectively.

The human CD4 minigene transgene is not expressed in mature CD8+ cells. The transgene includes a 4.5 kb fragment of the murine CD4 gene which has transcriptional enhancer activity restricted to T cells. An analogous human CD4 minigene lacking this enhancer element was not expressed in T cells. Transient transfection studies in CD8+CD4⁻ cell lines failed to demonstrate transcriptional silencing activity by the 0.3 kb minimal enhancer element contained within the 4.5 kb fragment, so a second element present in the 4.5 kb fragment may act to suppress transcription in cells which express only CD8.

The resultant transgenic mice homozygous for murine CD4 null alleles and concomitantly harboring a human CD4 transgene produce helper T cells which depend on the transgene-encoded human CD4 protein for development and function. Such transgenic mice are a useful experimental system for studying human diseases which involve CD4+ T cells, such as AIDS and autoimmunity, and for developing vaccines. For example, HIV-mediated viral pathogenesis in humans can involve an interaction between the virion envelope glycoprotein gp120 and human CD4 for viral entry and/or for the destruction of CD4+ helper T cells. Therapies designed to prevent this process are readily testable in this animal model.

CD4 knockout mice are bred with other knockout genotypes, particularly with MHC class II gene knockout mice, to generate mice having multiple knockout loci.

Example 3
Generation of CD2-Deficient Mice

The CD2 glycoprotein is an adhesion molecule that has been shown to transduce mitogenic signals in T cells (Moingeon et al. (1989) *Immunol. Rev.* 111: 111; Dustin M. L. and Springer T. A. (1991) *Ann. Rev. Immunol.* 9: 27, incorporated herein by reference). Numerous studies have demonstrated inhibition of T cell function and adhesion by monoclonal antibodies specific for CD2, indicating that this molecule has an important role in the immune response. CD2 likely plays a key role in T cell differentiation, as it is expressed early in thymocyte ontogeny and may be involved in thymocyte binding to thymic epithelium. The CD2 molecule, also known as T11, LFA-2, or the E-receptor binds to the widely-expressed CD58 (or LFA-3) glycoprotein. In mice CD2 is a 55–60 kD glycoprotein expressed on the surface of T cells, B cells, and NK cells. In humans, CD2 is not expressed on B-cells. It has been proposed that the binding of CD2 to CD58 is important in the stabilization of conjugates between T cells and their targets, thereby facilitating the generation of an effective immune response (Williams A. F. and Beyers A. D. (1992) *Nature* 356: 746). Appropriate combinations of antibodies against CD2 cause T cell mitogenesis (Meuer et al. (1984) *Cell* 36: 897). Intracellular signals delivered through CD2 mimic those observed when the T cell antigen receptor (TCR/CD3) is engaged by antibodies or antigen/MHC (Moingeon et al. (1989) op.cit.; Ley et al. (1991) *Eur. J. Immunol.* 21: 2203). T cell activation through CD2 may involve direct interactions with components of the TCR/CD3 complex. Variants of the Jurkat T leukemic cell line lacking CD2 have a diminished capacity to produce IL-2 in response to TCR or CD3 ligation, but the defect can be corrected by transfection of a CD2 transgene (Makni et al. (1991) *J. Immunol.* 146: 2522). Co-precipitation of the TCR with antibodies against CD2 indicates that CD2 appears to be an integral participant in the recognition of antigen by the TCR/CD3 complex (Beyers et al. (1992) op.cit.).

Human CD2 may also be involved in HIV-1 pathogenesis (Laurence et al. (1992) *Nature* 358: 255; Cameron et al.

(1992) *Science* 257: 383; Siciliano et al. (1988) *Cell* 54: 561; Mittler R. S. and Hoffman M. K. (1989) *Science* 246: 1380).

To inactivate the murine CD2 gene, D3 ES cells (Doetschman et al. (1985) op.cit.) were were transfected with the linearized targeting construct shown in FIG. 10. This construct introduces a neo resistance gene into a PstI site in the second exon of the murine CD2 gene, thereby disrupting the sequence encoding the amino-terminal V-like domain.

Figure 10:
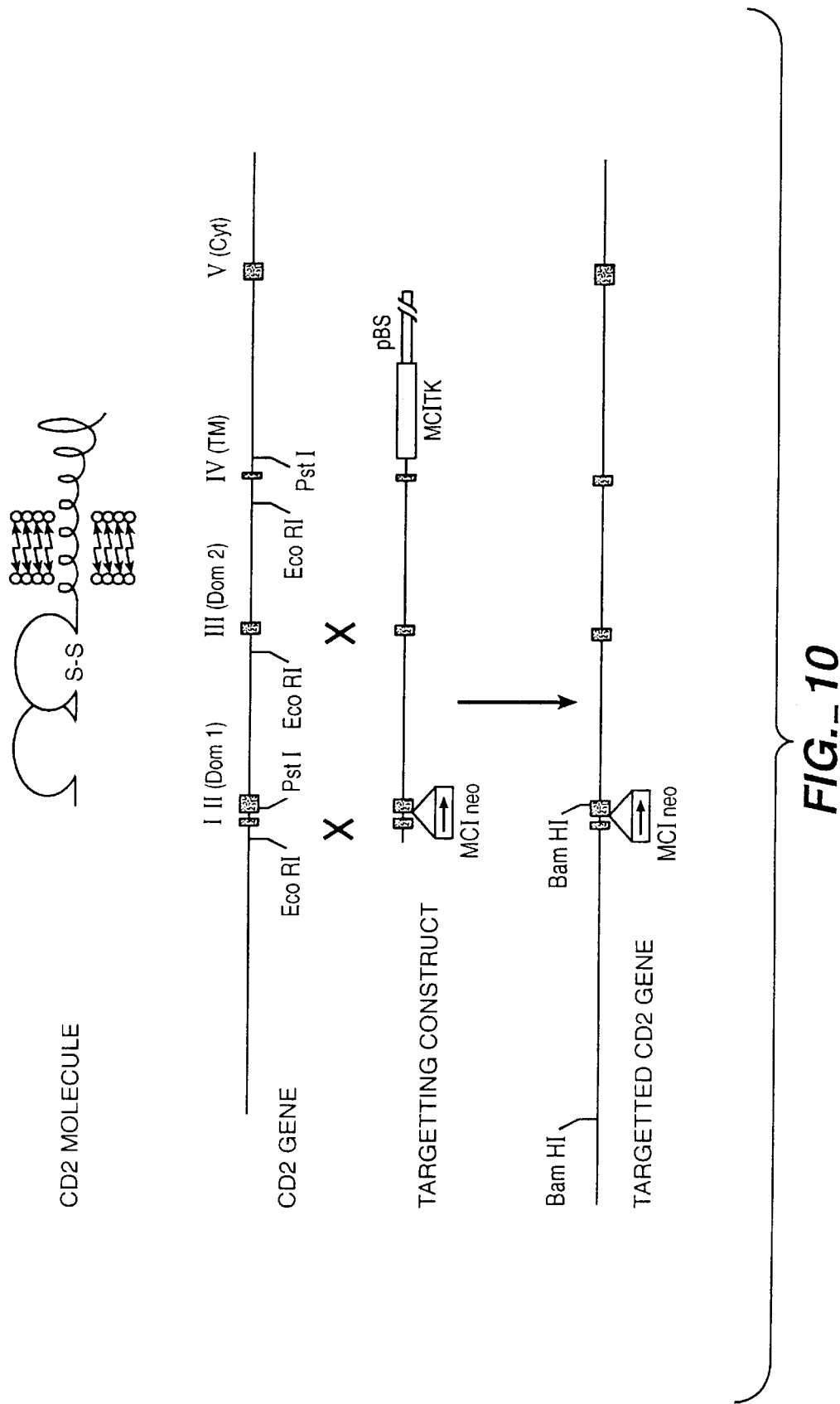
FIG. 10 shows a schematic of the murine CD2 transmembrane protein and a map of the murine CD2 gene locus and a targeting construct for functionally disrupting the murine CD2 gene by targeted homologous recombination.

The CD2 targeting construct was constructed using a CD2 genomic clone isolated from a murine genomic library provided by Dr. Glenn Evans (Salk Institute, LaJolla, Calif.), and available upon request. The cloning of the murine CD2 gene has been reported (Sewell et al. (1987) *Eur. J. Immunol.* 17: 1015, incorporated herein by reference). The plasmids pMC1neopolyA (Stratagene, San Diego, Calif.) and pIC19R/MC1-TK (from Dr. Kirk Thomas, University of Utah, Salt Lake City, Utah) were also used. The neo positive selection expression cassette was purified from the pMC1neopolyA plasmid by restriction digestion and ligated into the PstI site of the cloned murine CD2 gene, and the tk negative selection expression cassette was purified from pIC19R/MC1-TK and ligated to the downstream portion of the CD2 genomic clone to form a CD2 targeting construct as shown in FIG. 10.

D3 ES cells were grown according to the protocols described by Robertson E. J. (1987) op.cit. except that the culture medium was 15% fetal calf serum with no additional newborn calf serum. $2 \times 10^7$ cells were transfected by electroporation with 20–25 $\mu$g of the ClaI-linearized CD2-targeting construct by electroporation in 0.8 ml of PBS at 250 V/500 $\mu$F. $5 \times 10^6$ cells were seeded on 10 cm plates containing $4 \times 10^6$ mitomycin C-inactivated G418$^R$ STO feeder cells. Selection with 150 $\mu$g/ml of G418 was imposed after 36 hours, and gancyclovir was not used for negative selection. Colonies were transferred into 96-well plates containing feeder cells after 12–14 days, at which time selection was removed. Two days later, each colony was split in two parts; half of each clone was returned to culture while the rest was used in pools of 10–30 clones for PCR analysis. DNA was extracted from these pools according to a modification of the protocol described by Bowtell (1987) *Anal. Biochem.* 163: 391, incorporated herein by reference). Briefly, the cells were pelleted and resuspended in a small volume of PBS. 7–10 volumes of 6M guanidine hydrochloride/0.1M CH$_3$COONa were added and the mixture was rotated for 1 hour before precipitating with ethanol and resuspending the DNA in TE at 55° C. (1–2 hours) and 95° C. (10 minutes). PCR was performed for 35 cycles with denaturation for 1 minute at 94° C., annealing at 55° C. for 1 minute, and extension at 72° C. for 3 minutes. PCR positive pools were expanded and reanalyzed in smaller pools until the individual clones contributing the positive PCR signal were identified. Approximately 1 in 50 G418$^R$ colonies was found to have the CD2 gene disrupted. DNA was extracted for Southern blot analysis, and the remaining cells were frozen at the earliest possible passage.

Figure 11:
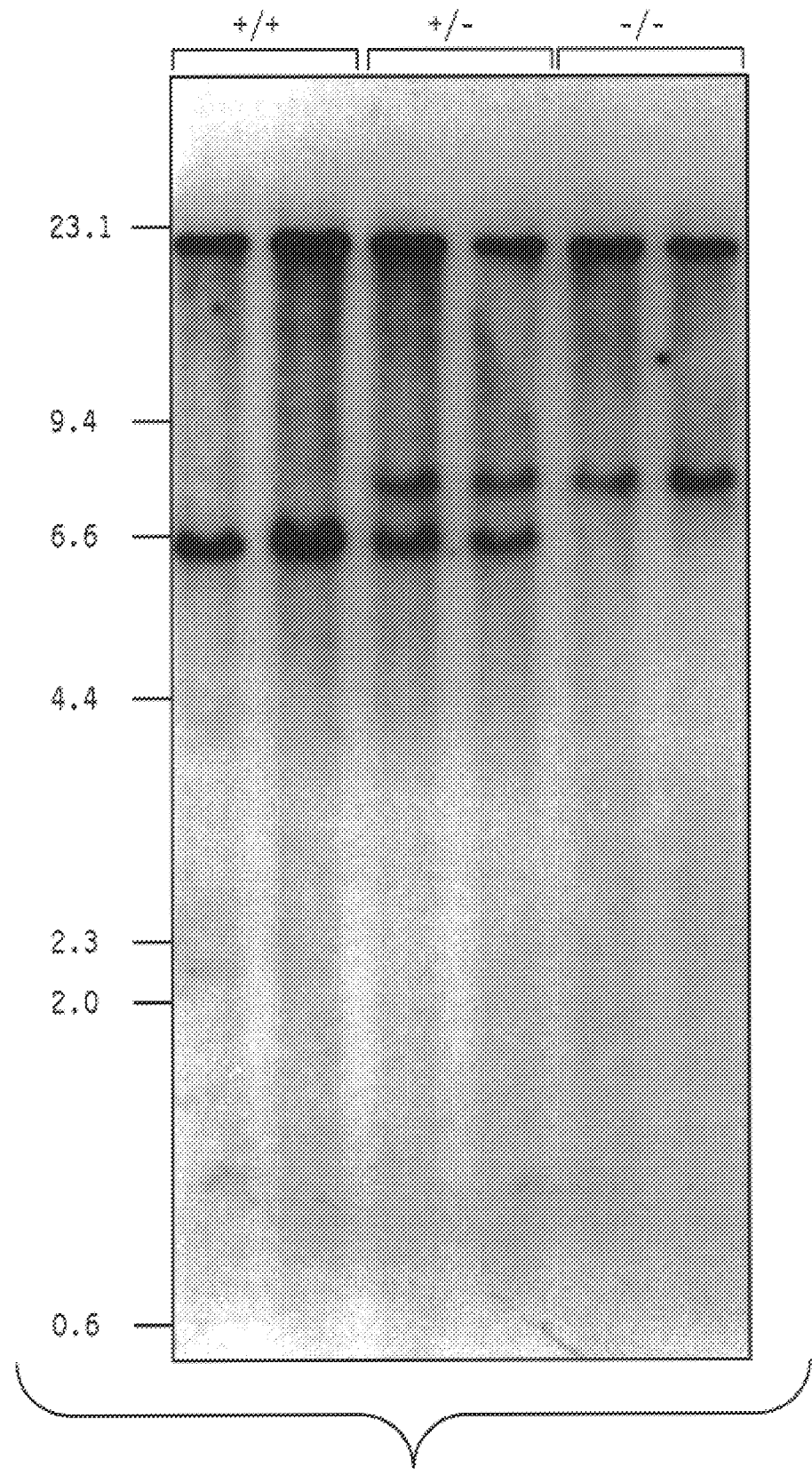
FIG. 11 shows a genomic Southern blot analysis of DNA from CD2-mutant and wild-type mice. The 1.2 kb insertion event was detected with a cDNA probe which spans the entire coding region and hybridizes to two BamHI fragments.

Blastocysts were harvested from C57BL/6 mice approximately 3.5 days post-coitus. The blastocysts were injected with correctly-targeted ES cells as described by Bradley A in *Teratocarcinomas and Embryonic Stem Cells: A Practical Approach* op.cit. and Hogan et al. *Manipulating the Mouse Embryo: A Laboratory Manual* op.cit. Injected balstocysts were reimplanted into the uteri of pseudopregnant C57BL/6xDBA/2 females. Chimeric progeny were identified by their coat color and the males were mated to C57BL/6xDBA/2 females. Germline transmission of the agouti marker and the neo gene identified mice carrying the functionally disrupted CD2 null allele, and these mice were intercrossed to produce homozygous null mice. Screening of the mice for the CD2 null allele was achieved by PCR, Southern blot, or by FACS analysis of peripheral blood for CD2 which can identify all genotypes. Intercrosses generated mice homozygous for the null CD2 allele at the expected Mendelian frequency. The structure of the targeted CD2 locus was examined by Southern blot analysis using a CD2 cDNA probe (FIG. 11), a pMC1neo probe (not shown), and a probe upstream of the region encompassed by the targeting construct (not shown) on several different digests of genomic DNA from ES cells and mice of various genotypes. In all cases, the observed bands were consistent with the pattern expected from the map shown in FIG. 10.

Figure 12:
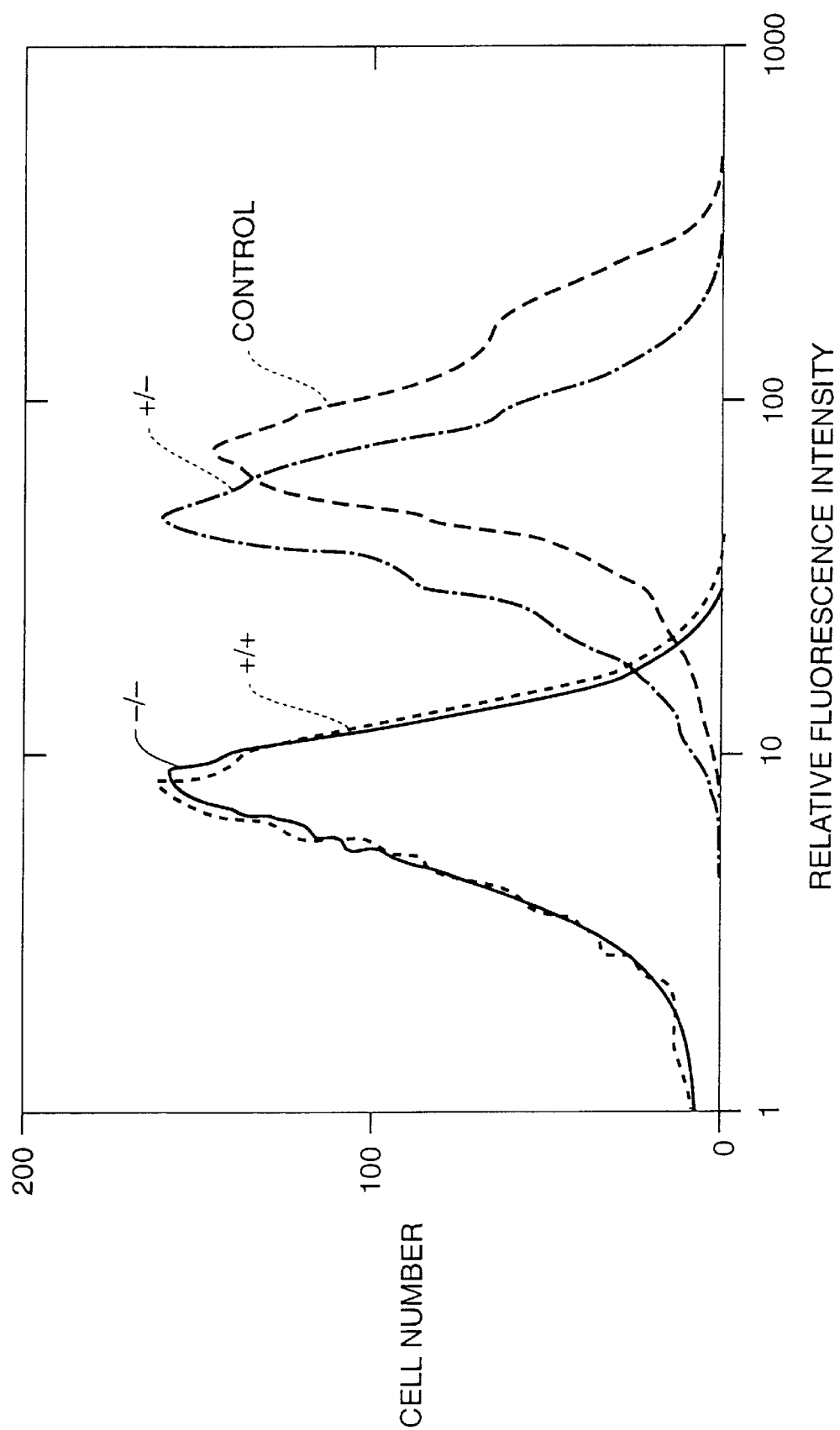
FIG. 12 shows the absence of cell surface CD2 in CD2 knockout mice. Thymocytes were stained with the anti-CD2 monoclonal antibody RM2-5 and fluorescein-conjugated goat anti-mouse IgG-Fc. Ten-thousand gated events were collected using the FAScan.

Mice homozygous for the CD2 disruption (CD2–/–) have remained consistently healthy for more than 40 weeks. Lymphocytes from these mice do not stain with a panel of 5 different anti-CD2 monoclonal antibodies, and lymphocytes from heterozygous CD2 knockout mice (CD2+/–) show a two-fold drop in fluorescent intensity relative to wild-type (CD2+/+), as shown in FIG. 12.

Figure 13:
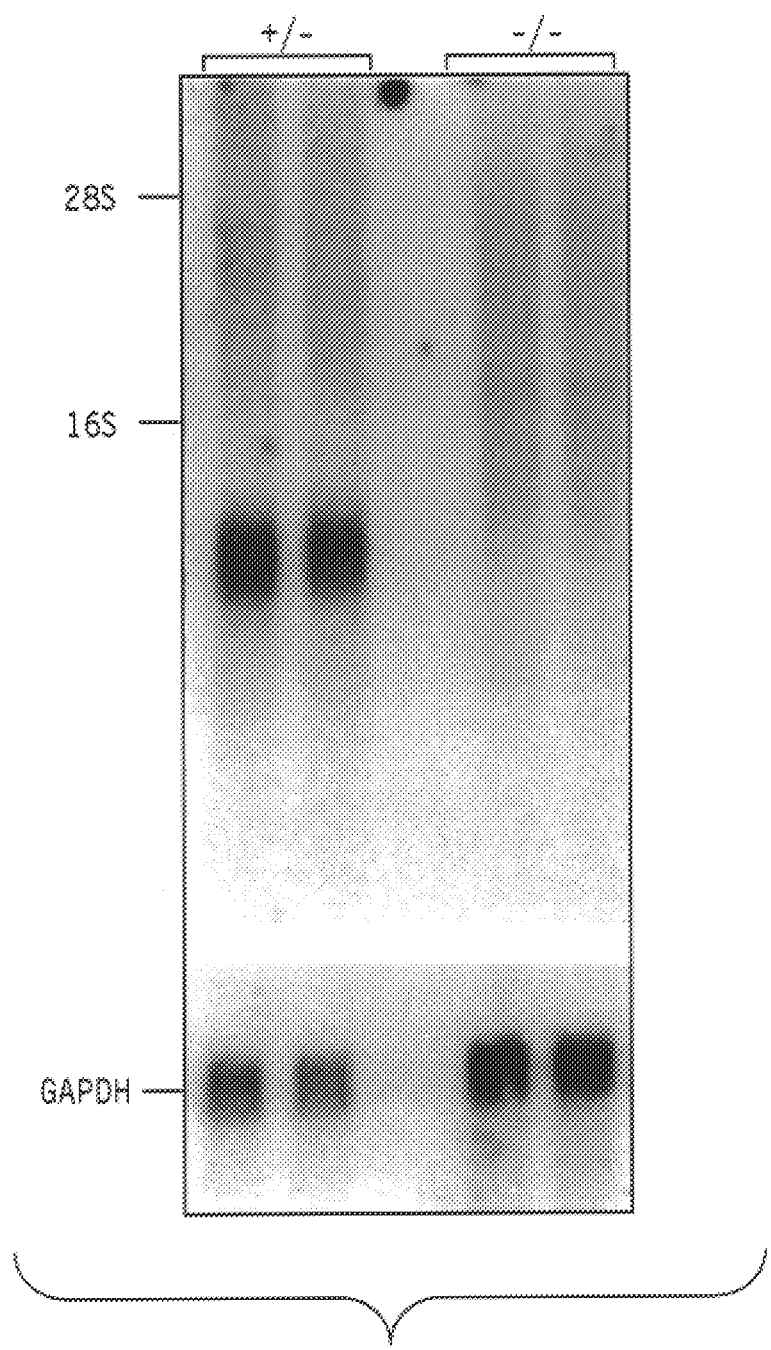
FIG. 13 shows a Northern blot indicating the absence of CD2 mRNA in CD2 knockout mice. RNA was isolated from thymuses and lymph nodes of CD2–/– and +/+ mice and probed with a murine CD2 cDNA.

Northern blotting was used to assess the efficacy of the CD2 disruption on CD2 transcripts. As shown in FIG. 13, , strong hybridization to a CD2 cDNA probe was obtained with RNA from CD2+/+ thymocytes and peripheral lymphocytes, but no detectable signal was observed with cells from homozygous knockout mice (CD2–/–), despite control hybridization to a GAPDH probe. This loss of CD2 hybridization may be due to efficient utilization of the pMC1neo polyadenylation signal which would terminate any RNA transcript before the bulk of the CD2 structural sequence. Alternatively, the pMC1 promoter/enhancer may interfere with transcription initiating at the endogenous CD2 gene promoter or may cause RNA instability.

The foregoing description of the preferred embodiments of the present invention has been presented for purposes of illustration and description. They are not intended to be exhaustive or to limit the invention to the precise form disclosed, and many modifications and variations are possible in light of the above teaching.

Such modifications and variations which may be apparent to a person skilled in the art are intended to be within the scope of this invention.

All publications and patent applications herein are incorporated by reference to the same extent as if each individual publication or patent application was specifically and individually indicated to be incorporated by reference.

We claim:

1. A transgenic mouse comprising a diploid genome having a functionally disrupted endogenous CD4 gene, wherein said disruption is in the nucleotide sequence of one or more coding region exons, and having integrated into its genome a gene encoding human CD4, wherein said human CD4 gene is transcriptionally regulated by an operably linked human CD4 promoter and upstream T cell specific enhancer and wherein said mouse expresses human CD4 protein in a T cell specific manner.

2. The transgenic mouse of claim 1 wherein said mouse is homozygous for the functionally disrupted endogenous murine CD4 gene.

3. The transgenic mouse of claim 2 where said mouse is capable of germline transmission of the functionally disrupted endogenous CD4 locus.

4. The transgenic mouse of claim 3 wherein said mouse further comprises an integrated transgene encoding human CD4 protein and wherein said mouse is capable of germline transmission of said transgene.

5. The transgenic mouse of claim 2 wherein the transgenic mouse expresses a human CD4 protein on peripheral CD8-T cells and does not express detectable human CD4 protein on peripheral CD8+ T cells.

6. The transgenic mouse of claim 2 wherein the mouse has a peripheral lymphocyte population wherein surface expression of human CD4 on lymphocytes having a mouse genome is detectable and surface expression of mouse CD4 on said lymphocytes is undetectable.

7. The transgenic mouse of claim 4 wherein said transgenic mouse expresses a human CD4 protein on peripheral CD8-T cells and does not express detectable levels of human CD4 protein on peripheral CD8+ cells.

8. The transgenic mouse of claim 1 wherein said CD4 gene is a primate CD4 gene.

* * * * *

UNITED STATES PATENT AND TRADEMARK OFFICE
CERTIFICATE OF CORRECTION

PATENT NO. : 5,859,312

DATED : January 12, 1999

INVENTOR(S) : Daniel Littman, Shinichiro Sawada, and Nigel Killeen

It is certified that error appears in the above-identified patent and that said Letters Patent is hereby corrected as shown below:

Column 1, line 5,

This invention was made with government support under Grant No. R01 AI23513 awarded by the National Institutes of Health. The Government has certain rights in this invention.

Signed and Sealed this

Fourth Day of January, 2000

Attest:

Attesting Officer

*Acting Commissioner of Patents and Trademarks*